(12) United States Patent
Susaki et al.

(10) Patent No.: US 6,835,807 B1
(45) Date of Patent: Dec. 28, 2004

(54) DRUG COMPLEX AND DRUG DELIVERY SYSTEM

(75) Inventors: Hiroshi Susaki, Chiba (JP); Kazuhiro Inoue, Chiba (JP); Hiroshi Kuga, Tokyo (JP)

(73) Assignee: Daiichi Pharmaceuticals Co., Ltd., Tokyo (JP)

( * ) Notice: Subject to any disclaimer, the term of this patent is extended or adjusted under 35 U.S.C. 154(b) by 0 days.

(21) Appl. No.: 09/674,526

(22) PCT Filed: May 21, 1999

(86) PCT No.: PCT/JP99/02681

§ 371 (c)(1),
(2), (4) Date: Feb. 13, 2001

(87) PCT Pub. No.: WO99/61061

PCT Pub. Date: Dec. 2, 1999

(30) Foreign Application Priority Data

May 22, 1998 (JP) .......................................... 10/140915

(51) Int. Cl.[7] .......................... A61K 9/00; A61K 31/47; A61K 47/36; A61K 47/48; C07D 491/22

(52) U.S. Cl. ............................... 530/322; 514/2; 514/8; 514/18; 514/54; 514/59; 514/283; 514/613; 514/616; 530/330; 530/345; 536/112; 536/123.1; 546/51; 564/153; 564/155; 564/193

(58) Field of Search ........................... 514/2, 8, 12, 16, 514/17, 18, 19, 21, 25, 54, 59, 283, 613, 616; 530/322, 328, 329, 330, 331, 345, 409; 536/112, 123.1; 564/153, 155, 193; 525/54.1; 546/51

(56) References Cited

U.S. PATENT DOCUMENTS

| | | | |
|---|---|---|---|
| 5,688,931 A | 11/1997 | Nogusa et al. ................. | 536/20 |
| 5,892,043 A | 4/1999 | Tsujihara et al. .............. | 546/48 |
| 6,368,598 B1 * | 4/2002 | D'Amico et al. ......... | 424/181.1 |
| 6,512,118 B1 | 1/2003 | Tsujihara et al. .............. | 546/48 |
| 6,617,456 B1 | 9/2003 | Tsujihara et al. .............. | 546/48 |

FOREIGN PATENT DOCUMENTS

| | | |
|---|---|---|
| EP | 624377 A2 * | 11/1994 |
| EP | 0781781 | 7/1997 |
| EP | 916348 A1 * | 5/1999 |
| JP | 6-87746 | 3/1994 |
| JP | 7-84481 | 9/1995 |
| JP | 11-71280 | 3/1999 |
| JP | 11-92405 | 4/1999 |
| WO | 92/14759 | 9/1992 |
| WO | 94/19376 | 9/1994 |
| WO | 97/46260 | 12/1997 |
| WO | 98/13059 | 4/1998 |
| WO | WO 98/19705 A1 * | 5/1998 |

OTHER PUBLICATIONS

English Language Abstract of JP 6–87746 (Mar. 29, 1994).
English Language Abstract of JP 11–92405 (Apr. 6, 1999).
Abstracts of 10th Meeting of the Japan Society of Drug Delivery System, pp. 279 (1994).
Abstracts of 9th Annual Meeting of Japanese Society for the Study of Xenobiotics, pp. 292 (1994).
Abstracts of 19th Seminar of Trends in Research and Development, pp. D–9—D–12 (1995).
Abstracts of 12th Colloid and Interface Technology Symposium, The Chemical Society of Japan, pp. 51–58 (1995).
Gene M. Dubowchik et al., "Monomethoxytrityl (MMT) as a Versatile Amino Protecting Group for Complex Prodrugs of Anticancer Compounds Sensitive to Strong Acids, Bases and Nucleophiles", Tetrahedron Letters, vol. 38, No. 30, pp. 5257–5260 (1997).
Gene M. Dubowchik et al., "Efficient Mitomycin C Coupling With Stable p–Nitrophenyl–Benzyl Carbonates Using N–Hydroxybenzotriazole as a Catalytic Additive", Tetrahedron Letters, vol. 38, No. 30, pp. 5261–5264 (1997).
Gene M. Dubowchik et al., "Cathepsin B–Sensitive Dipeptide Prodrugs.1. A Model Study of Structural Requirements for Efficient Release of Doxorubicin", Bioorganic & Medicinal Chemistry Letters, vol. 8, pp. 3341–3346 (1998).
Gene M. Dubowchik et al., "Cathepsin B–Sensitive Dipeptide Prodrugs.2. Models of Anticancer Drugs Paclitaxel (Taxol®), Mitomycin C and Doxorubicin", Bioorganic & Medicinal Chemistry Letters, vol. 8, pp. 3347–3352 (1998).
Franciscus M.H. de Groor et al., "Synthesis and Biological Evaluation of Novel Prodrugs of Anthracyclines for Selective Activation by the Tumor–Associated Protease Plasmin", J. Med. Chem., vol. 42, pp. 5277–5283 (1999).
Ion Niculescu–Duvaz et al., "Self–Immolative Anthracycline Prodrugs for Suicide Gene Therapy", J. Med. Chem., vol. 42, pp. 2485–2489 (1999).
Dan Niculescu–Duvaz et al., "Self–Immolative Nitrogen Mustard Prodrugs for Suicide Gene Therapy", J. Med. Chem., vol. 41, pp. 5297–5309 (1998).

(List continued on next page.)

Primary Examiner—Jeffrey Edwin Russel
(74) Attorney, Agent, or Firm—Greenblum & Bernstein, P.L.C.

(57) ABSTRACT

A drug complex useful as a DDS compound, which is represented by the following formula: A-R—NH—Y—$CH_2$—O—CO-Q, wherein A is a polymer as a drug carrier; R is a spacer, wherein the spacer is an amino acid or an oligopeptide comprising 2 to 8 amino acids; Y is phenylene group which may be substituted; and Q is a residue of a drug compound such as antineoplastic agents. The complex provides rapid and site-selective release of a drug compound such as antineoplastic or anti-inflammatory agents and surely exhibits expected efficacy.

20 Claims, 6 Drawing Sheets

OTHER PUBLICATIONS

Richard B. Greenwald et al., "Drug Delivery Systems Employing 1.4– or 1,6–Elimination: Poly(ethylene glycol) Prodrugs of Amine–Containing Compounds", J. Med. Chem., vol. 42, pp. 3657–3667 (1999).

Yu–Ling Leu et al., Design and Synthesis of Water–Soluble Glucuronide Derivatives of Camptothecin for Cancer Prodrug Monotherapy and Antibody–Directed Enzyme Prodrug Therapy (ADEPT), J. Med. Chem., vol. 42, pp. 2623–2628 (1999).

Ruben G.G. Leenders et al., "Novel Anthracycline–spacer–β–glucuronide, –β–glucoside, and –β–galactoside Prodrugs for Application in Selective Chemotherapy", Bioorganic & Medicinal Chemistry, vol. 7, pp. 1597–1610 (1999).

T.W. Greene et al., Protective Groups in Organic Synthesis, 2nd Ed., John Wiley & Sons, Inc. (1991) pp. 60–62, 318–319 and 327–329.

Patent Abstracts of Japan vol. 1999, No. 08, Jun. 30, 1999, for JP 11–71280.

* cited by examiner

DRUG COMPLEX AND DRUG DELIVERY SYSTEM

TECHNICAL FIELD

The present invention relates to a drug complex in which a drug carrier such as polysaccharide derivatives and a drug compound such as antineoplastic agents are bound to each other via a spacer.

BACKGROUND ART

Antineoplastic agents, used for treatment of solid cancers such as lung cancer or digestive organ carcinomas and blood cancers such as leukemia, are systemically administered through routes of administration such as intravenous or oral administration, and then, are distributed to certain tumorous sites and inhibit or suppress the proliferation of cancer cells to exhibit their therapeutic efficacy. However, the systemically-administered antineoplastic agents are rapidly taken into livers and reticuloendothelial organs from blood, or rapidly excreted into urine, and accordingly, their blood concentrations may sometimes be lowered to render the distribution into tumorous sites insufficient. In addition, antineoplastic agents ordinarily used have poor distribution selectivity to tumorous sites (tumor selectivity), and therefore, the antineoplastic agents are uniformly distributed over various tissues and cells of the whole body and act as cytotoxins also against normal cells and tissues, which results in problems of the appearance of adverse effects, e.g., emesis, pyrexia, or alopecia at an extremely high rate. Therefore, it has been desired to develop antineoplastic agents which distribute efficiently and selectively to tumorous sites.

As one of such means, a process was proposed in which a polysaccharide derivative having carboxyl groups is used as a drug carrier, and an antineoplastic agent is bound to the polysaccharide derivative to delay the disappearance of the antineoplastic agent from blood and to enhance selectivity to tumor tissues. For example, International Publication WO94/19376 discloses a drug complex in which a peptide chain (the number of amino acid residues: 1 to 8) is bound to a carboxyl group of a polysaccharide having carboxyl groups, and doxorubicin, daunorubicin, mitomycin C, bleomycin or the like is further bound by means of the peptide chain. In addition, Japanese Patent Publication (KOKOKU) No. (Hei) 7-84481/1995 discloses a drug complex in which the aforementioned antineoplastic agent is introduced into a carboxymethylated mannoglucan derivative using a Schiff base or an acid amide bond. These drug complexes have more excellent antineoplastic activity, and reduced toxicity and adverse effects compared to antineoplastic agents, per se, that are bound to drug carriers.

There are some reports relating to drug complexes utilizing polyalcoholized polysaccharide derivatives as drug carriers, for example, "Researches on polysaccharide-peptide-doxorubicin complexes—Correlations between stabilities of polysaccharide carriers in blood and their antineoplastic activities" Abstracts of 10th Meeting of the Japan Society of Drug Delivery System, 279, 1994); "Researches on polysaccharide-peptide-doxorubicin complexes—Pharmacokinetics and antineoplastic activity" (Abstracts of 9th Annual Meeting of Japanese Society for the study of xenobiotics, 292, 1994); Abstracts of 19th Seminar of Trends in Research and Development (held by the organization for Pharmaceutical Safety and Research), D-9, 1995; and "Researches on drug delivery to a tumor tissue by polysaccharide carriers" (Abstracts of 12th Colloid and Interface Technology Symposium, The Chemical Society of Japan, 51, 1995). In addition, reagents comprising p-aminobenzyloxycarbonyl group and peptide group were developed as a technology for binding antineoplastic agents to antibodies and the like (Dubowchik, G. M., Tetrahedron Lett., 38, 5257, 5261, 1997). However, application to drug complexes having drug carriers as described above has not been known.

DESCRIPTION OF THE INVENTION

The inventors of the present invention made intensive studies on drug complexes in which a drug carrier such as polysaccharide derivatives and a drug compound such as antineoplastic agents are bound to each other via a spacer comprising 1 to 8 amino acids, thereby successfully providing a drug complex which can site-selectively distribute the drug compound such as antineoplastic agents to target tissues (International Publication WO97/46260). However, the inventors found that a releasing rate of a drug compound from a drug complex, which comprises a spacer comprising 1 to 8 amino acids, is occasionally independent of the rate of enzymatic degradation (hydrolysis by peptidase) of the spacer moiety, and the releasing rate may sometimes be affected by the steric structure of the drug compound. Especially where the binding moiety between the reactive functional group (e.g., amino group) of the drug compound and the spacer has steric hindrance, the tendency was found to be highly remarkable. In addition, when such drug complexes are used, drug compounds are sometimes released by enzymatic degradation of the spacer which have one or a few residual amino acids derived from the spacer, thereby irregular release of the drug compound is sometimes caused.

Accordingly, an object of the present invention is to provide a drug complex formed by binding a drug compound such as antineoplastic agents and antiinflammatory agents to a drug carrier via a spacer comprising 1 to 8 amino acids, which can site-selectively distribute the active ingredient to tumorous sites and the like and in which the releasing rate of the drug compound substantially depends on the rate of enzymatic degradation of the spacer moiety. In addition, another object of the present invention is to provide a drug complex in which the releasing rate or the drug compound is not substantially affected by the steric structure of the drug compound, and a releasing rate of the drug compound can be achieved which is expected from the rate of enzymatic degradation of the spacer moiety.

The inventors of the present invention made intensive studies to achieve the aforementioned objects. As a result, they found that, in drug complexes formed by binding a drug compound such as antineoplastic agents and anti-inflammatory agents to a drug carrier via a spacer comprising 1 to 8 amino acids, further insertion of aminobenzyloxycarbonyl group and the like between the spacer and the drug compound causes immediate non-enzymatic hydrolysis of the aminobenzyloxycarbonyl group after enzymatic hydrolysis of the spacer moiety to release the drug compound. They also found that, in the aforementioned drug complex, the releasing rate of the drug compound is not affected by the steric structure of the drug compound and substantially depends on the rate of enzymatic degradation of the spacer moiety. The present invention was achieved on the basis of these findings. The drug complex of the present invention is characterized in that the releasing rate of the drug 3% compound can be controlled on the basis of the rate of enzymatic degradation of the spacer moiety, regardless of the steric structure of the drug compound.

The present invention thus provides a drug complex represented by the following formula (I):

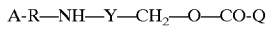

wherein A is a polymer as a drug carrier; R is a spacer, wherein said spacer is an amino acid or an oligopeptide comprising 2 to 8 amino acids; Y is phenylene group which may be substituted; and Q is a residue of a drug compound. The drug complex is useful, for example, as a DDS (drug delivery system) compound having the DDS function.

According to another aspect of the present invention, we, inventors, found a compound represented by the following formula: R'—NH—Y—CH$_2$O—CO-Q, wherein R'— is a group which comprises one amino acid or peptide-bonded 2 to 8 amino acids and of which N-terminal is protected or not protected; Y is phenylene group which may be substituted; and Q is a residue of a drug compound; and a compound represented by the following formula: A-R—NH—Y—CH$_2$—O—CO—X, wherein A is a polymer as a drug carrier; R is a spacer, wherein said spacer is an amino acid or au oligopeptide comprising 2 to 8 amino acids; Y is phenylene group which may be substituted; and X is selected from the group comprising hydroxyl group, —O-M wherein M is a protective group for carboxyl group, or an eliminating group. These compounds are useful as synthetic intermediates for the manufacture of the aforementioned drug complex.

According to preferred embodiments of the present invention, we found the above drug complex wherein the drug carrier is a polysaccharide derivative having carboxyl groups; the above drug complex wherein R is a spacer comprising peptide-bonded 2 to 8 amino acids; the above drug complex wherein Y is p-phenylene group which may be substituted; the above drug complex wherein Y is unsubstituted p-phenylene group; the above drug complex wherein the polysaccharide derivative having carboxyl groups is a carboxy($C_{1-4}$)alkyldextran polyalcohol; the above drug complex wherein dextran polyalcohol that constitutes the carboxy($C_{1-4}$)alkyldextran polyalcohol is dextran polyalcohol which is obtained by treating dextran under conditions that enable substantially complete polyalcoholization; the above drug complex wherein the carboxy($C_{1-4}$)alkyldextran polyalcohol is carboxymethyldextran polyalcohol; the above drug complex wherein the drug compound is an antineoplastic agent or an anti-inflammatory agent; the above drug complex wherein A-R—NH—Y—CH$_2$O—CO— and an amino group of the drug compound are bound to each other; and the above drug complex wherein the drug compound is (1S,9S) 1-amino-9-ethyl-5-fluoro 2,3-dihydro-9-hydroxy-4-methyl-1H, 12H-benzo[de]pyrano[3',4':6,7]indolizino[1,2-b]quinoline-10,13-(9H,15H)-dione.

BEST MODE FOR CARRYING OUT THE INVENTION

Figure 1:
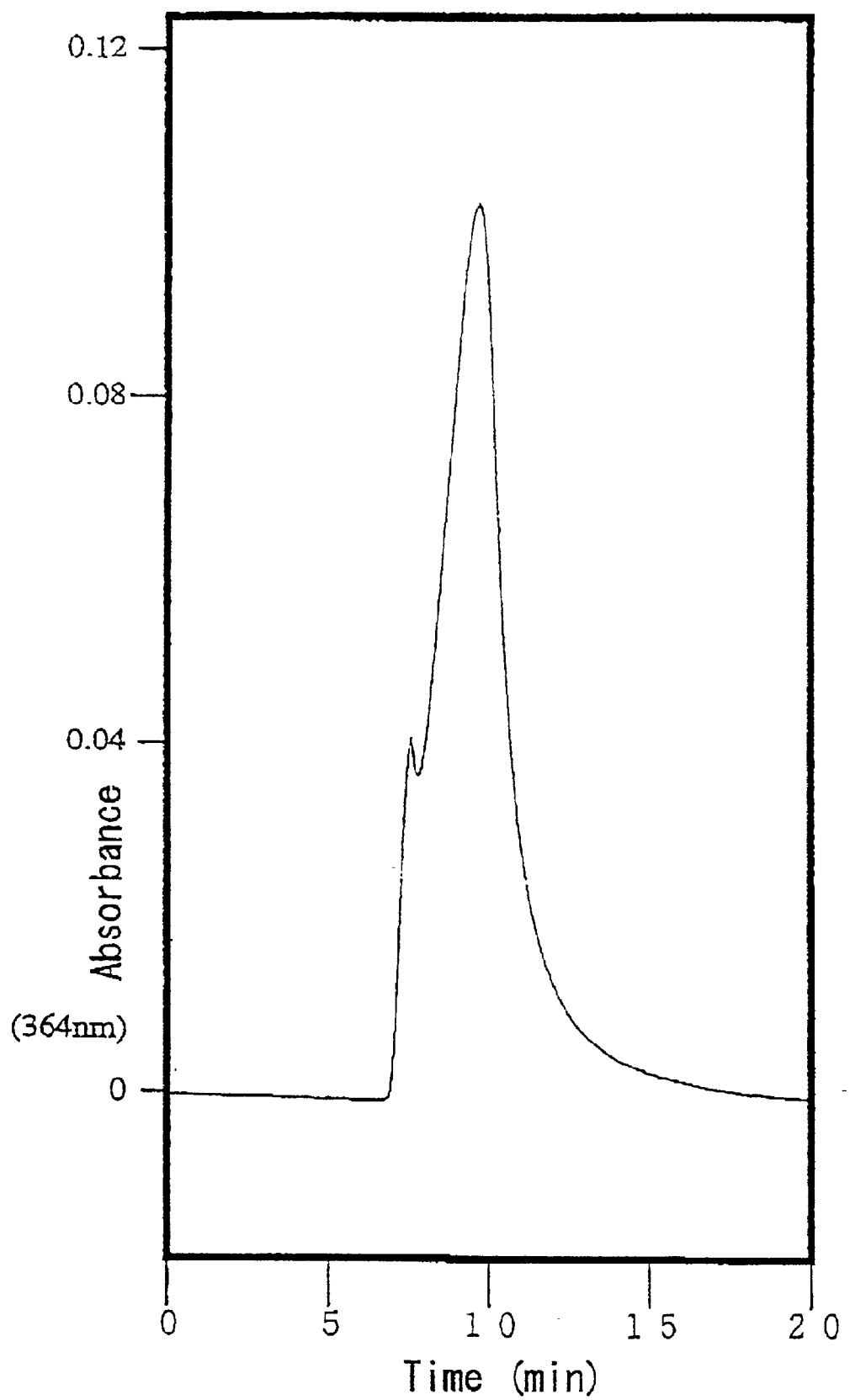
FIG. 1 shows a GPC (gel permeation chromatography) chart of the drug complex of the present invention (Example 1).

The drug complex provided by the present invention is represented by formula (I): A-R—NH—Y—CH$_2$O—CO-Q. In the formula, Q represents a residue of a drug compound. The residue of the drug compound contained in the drug complex according to the present invention is a main partial structure derived from a drug compound used for therapeutic and/or preventive treatment of diseases of mammals including humans, for example, an antineoplastic agent, an anti-inflammatory agent, an antibacterial agent or the like, and the term means those containing at least an essential moiety for expression of the pharmacological activity of the drug compound. However, the drug compound from which the residue is derived is not limited to those mentioned above. As the drug compound, any compounds may be used so long as they have one or more reactive functional groups capable of participating in bond formation with the carbonyl group of the group represented by A-R—NH—Y—CH$_2$—O—CO— (for example, amino group, carboxyl group, hydroxyl group, thiol group, ester group or the like). The term "drug compound" used in the present specification also includes a prodrug compound which contains, as a part thereof, a major structure of a drug compound having pharmacological activity, per se, and can reproduce the compound in vivo.

The term "residue of a drug compound" used in the present specification means a partial structure derived from the drug compound existing in the drug complex after bond formation, assuming that a bond between a carbonyl group of the group represented by A-R-NH—Y—CH$_2$—O—CO— and the residue of a drug compound is formed through a reaction of a reactive functional group of the drug compound and a carboxyl group of the group represented by A-R—NH—Y—CH$_2$—O—COOH (e.g., dehydration condensation and the like). For example, when the drug compound is represented by D-NH$_2$, D-NH-D', D-OH, or D-SH, the residue of the drug compound is represented by D-NH—, D-N(D')—, D-O—, or D-S—, respectively, and the drug complex using these drug compounds is represented by A-R—NH—Y—CH$_2$—O—CO—NH-D, A-R—NH—Y—CH$_2$—O—CO—N(D')-D, A-R—NH—Y—CH$_2$—O—CO—O-D, or A-R—NH—Y—CH$_2$—O—CO—S-D, respectively. However, the type of the bond between the group represented by A-R—NH—Y-CH$_2$—O—CO— and the residue of the drug compound is not limited to those mentioned above.

As the drug compound, for example, antineoplastic agents such as doxorubicin, daunorubicin, mitomycin C, bleomycin, cyclocytidine, vincristine, vinblastine, methotrexate, platinum antineoplastic agents (cisplatin or derivatives thereof), taxol or derivatives thereof, camptothecin or derivatives thereof (antineoplastic agents described in Japanese Patent Unexamined Publication (KOKAI) No. (Hei) 6-87746/1994, preferably (1S,9S)-1-amino-9-ethyl-5-fluoro-2,3-dihydro-9-hydroxy-4-methyl-1H,12H-benzo[de]pyrano[3',4':6,7]indolizino[1,2-b]-quinoline-10,13-(9H, 15H)-dione disclosed in claim 2 or the like) may preferably be used. In addition, steroidal anti-inflammatory agents such as hydrocortisone succinate and prednisolone succinate, and nonsteroidal anti-inflammatory agents such as mefenamic acid, flufenamic acid, diclofenac, ibuprofen, and tinoridine are also preferred.

As the phenylene group represented by Y, either of o-phenylene group or p-phenylene group may be used. When the phenylene group is substituted, the type, number and position of the substituents are not particularly limited.

Examples of the substituents which may exist on the ring of the phenylene group can include, for example, lower alkyl groups (i.e., linear or branched $C_{1-6}$ alkyl groups, cyclic $C_{3-6}$ alkyl groups, etc. Hereinafter the same applies to substituents containing lower alkyl moieties.), halo(lower alkyl) groups (e.g., chloromethyl group and trifluoromethyl group), hydroxy(lower alkyl) groups (e.g., hydroxymethyl group), lower alkoxyl groups (e.g., methoxy group and ethoxy group), lower alkenyl groups (e.g, vinyl group and allyl group), lower alkynyl groups (e.g, propargylic group), hydroxyl group, halogen atoms (any of fluorine atom, chlorine atom, bromine atom, and iodine atom), carboxyl group, alkoxycarbonyl groups (e.g., methoxycarbonyl group), alkanoyl groups (e.g., acetyl group), haloalkanoyl groups (e.g., trifluoroacetyl group), aryl groups (e.g, phenyl group and naphthyl group), aralkyl groups (eg., benzyl group), aryloxy groups (e.g., phenoxy group), aralkyloxy groups (e.g., benzyloxy group), aroyl groups (e.g., benzoyl group), heteroaryl groups (e.g., pyridyl group and quinolyl group), amino group, mono or di-(lower alkyl) amino groups, carbamoyl group, nitro group, cyano group, (lower alkyl) sulfinyl groups, (lower alkyl)sulfonyl groups, thiol group, (lower alkyl)thio groups and the like, and the substituent is not limited to those mentioned above.

When the phenylene group has two or more substituents on the ring, the substituents may be the same or different. The substituents may further have one or more functional groups. Specific examples of such substituents include chlorophenyl group, methylcarbamoyl group, chlorobenzyl group, alkoxybenzyl groups and the like. The phenylene group represented by Y is preferably substituted or unsubstituted p-phenylene group, most preferably unsubstituted p-phenylene group.

R represents a spacer. The term "spacer" used herein means a partial structure of the drug complex according to the present invention which exists between a polymer being a drug carrier and the residue of the drug compound, and is a moiety comprising one amino acid or 2 to 8 amino acids. The spacer plays a role to hold the residue of the drug compound in the drug carrier in tissues and blood where the drug compound should not be released, and to be enzymatically degraded to release the drug compound in tissues where the drug compound should be released (e.g., tumorous tissues). As the spacer, a spacer comprising one amino acid or a spacer comprising peptide-bonded 2 to 8 amino acids can be used. The spacer has a form of a residue of one amino acid, which means a residue obtained by removing one hydrogen atom and one hydroxyl group fom an amino group and a carboxyl group of the amino acid, respectively, or a residue of an oligopeptide comprising peptide-bonded 2 to 8 amino acids, which means a residue obtained by removing one hydrogen atom and one hydroxyl group from the N-terminal amino group and the C-terminal carboxyl group of the oligopeptide, respectively. The spacer is located so as to form a peptide-bond with NH—Y—CH$_2$—O—CO-Q at its C-terminal, or its carboxyl group when the spacer comprises one amino acid In general, the bond between the drug carrier represented by A and the spacer is formed by a peptide-bond between a carboxyl group of the drug carrier and the N-terminal of the oligopeptide spacer, or the amino group when the spacer comprises one amino acid. However, the bond between the spacer and the drug carrier is not limited to the aforementioned peptide bond, and may be another chemical bond or a bond using one or more spacers. For example, when one or more residues of dicarboxylic acid compounds (e.g., succinic acid) as building units are incorporated in a spacer so that the spacer has carboxyl groups at both ends, a reactive amino group in the drug carrier can be used for bond formation.

Preferred spacers are residues of oligopeptides comprising 2 to 6 amino acids. Kinds of amino acids constituting the spacer are not particularly limited, and for example, L- or D-amino acids, preferably L-amino acids can be used, and β-alanine, ε-aminocaproic acid, γ-aminobutyric acid or the like may also be used as well as α-amino acids. These amino acids other than α-amino acids are preferably located close to the drug carrier in the spacer.

Where a spacer comprising an oligopeptide is used, the amino acid sequence thereof is not particularly limited. Preferably used spacers include, for example, a spacer being a residue of a dipeptide represented by —X-Z-, wherein X represents a residue of a hydrophobic amino acid and Z represents a residue of a hydrophilic amino acid; and —X-Z- means a residue which consists of a dipeptide that is formed by a peptide bond between a hydrophobic amino acid (X) and a hydrophilic amino acid (Z) at the N-terminal side and the C-terminal side, respectively, and whose one hydrogen atom and one hydroxyl group are removed from the amino group at the N-terminal and the carboxyl group at the C-terminal, respectively, and a spacer containing a residue of the dipeptide as a partial peptide sequence. As the hydrophobic amino acid, for example, phenylalanine, tyrosine, leucine or the like can be used, and as the hydrophilic amino acid, for example, glycine, alanine or the like can be used. The spacer may have a repeated sequence of the dipeptide residues (for example, —X-Z-X-Z-, —X-Z-X-Z-X-Z- and the like).

By using the spacer containing such dipeptide structure, the spacer can be hydrolyzed in tumorous sites or inflammatory sites, which are considered abundant in peptidase, to release the drug compound at a high concentration in the sites within a short time. Accordingly, the partial structure formed by binding the spacer containing the above dipeptide and the bug compound to each other is a preferred partial structure of the drug complex according to the present invention. Where a residue of an antineoplastic agent exhibiting concentration-dependent antineoplastic activity (i e., an antineoplastic agent exhibiting more potent antineoplastic activity at a higher concentration thereof: a concentration-dependent antineoplastic agent. e.g., doxorubicin etc.) is used as the residue of the drug compound, a spacer composed of the above dipeptide residue represented by —X-Z- or a spacer containing the above dipeptide residue as a partial pep tide sequence may be preferably used.

Where an antineoplastic agent which requires a retained working time at over a certain concentration (e.g., methotrexate etc.) is used as the residue of the drug compound, enhanced antineoplastic activity may sometimes be obtained by using the above spacer. However, the spacers are not limited to those mentioned above in general, and it is necessary to choose an appropriate spacer from viewpoints of characteristics in pharmacokinetics and toxicity of the antineoplastic agent and the like. For carcinomas exhibiting rapid proliferation, it is generally preferred to choose the above spacer capable of releasing the drug compound at a high concentration in a short time. In particular, for the releasing rate of the drug compound in the drug complex according to the present invention, enzymatic degradation of the spacer moiety is the substantial rate-determining step. Accordingly, the desired releasing rate can easily be obtained by choosing an appropriate spacer from viewpoints of the enzymatic degradation rate.

Specific examples of the oligopeptide which can be used as the spacer are disclosed in Table 1 of Japanese Patent Unexamined Publication (KOKAI) No. 11-92405/1999. These oligopeptides can preferably be used as the spacer according to the present invention.

As the drug carrier represented by A, synthetic polymers and the like may be used as well as polysaccharide derivatives. Any polysaccharide derivatives and synthetic polymers may be used so long as they do not exhibit substantial toxicity against living bodies, and they can function as a drug carrier. For example, any polysaccharide derivatives and synthetic polymers that have conventionally been used for the production of drug complexes can be utilized for the drug complex of the present invention. For example, polysaccharide derivatives having carboxyl groups can preferably be used for the drug complex of the present invention, and polyalcoholized polysaccharide derivatives can most preferably be used. Examples of the synthetic polymer include, for example, polyethylene glycols; polyamino acids such as polyglutamic acids, polyaspartic acids and polylysines; and derivatives of polyvinyl compounds such as N-(2-hydroxypropyl)methacrylamide derivatives.

More specifically, any polysaccharide derivatives having carboxyl groups may be used so long as, for example, they are polysaccharides and derivatives thereof that are chemically or biologically modified and have carboxyl groups in their molecules. For example, polysaccharides such as hyaluronic acid, pectic acid, alginic acid, chondroitin, and heparin; and polysaccharides such as pullulan, dextran, mannan, chitin, inulin, levan, xylan, araban, mannoglucan, and chitosan in which all or a part of hydroxyl groups are introduced with functional groups having a carboxyl group can be used.

For example, those having carboxy($C_{1-4}$)alkylated hydroxyl groups or those having hydroxyl groups esterified with one of carboxyl groups of a polybasic acid can preferably be used. In addition, those obtained by polyalcoholizing the above polysaccharides and then introducing functional groups having a carboxyl group may also be used. The term "polysaccharide derivative" used in the present specification should be construed in its broadest sense, which includes polysaccharide compounds comprising saccharides as constitutional ingredients, and compounds obtained by partially or completely ring-opening a cyclic saccharide moiety of a polysaccharide compound (e.g., polyalcohol compounds etc.). Among these polysaccharide derivatives, carboxy($C_{1-4}$) alkyldextran polyalcohols, carboxy($C_{1-4}$) alkylpullulan polyalcohols and the like are preferably used. Specific explanations are given below with respect to examples wherein carboxy($C_{1-4}$)alkyldextran polyalcohols are used in the manufacture of the drug complex of the present invention. However, the drug carrier in the drug complex of the present invention is not limited to carboxy ($C_{1-4}$)alkyldextran polyalcohols.

The degree of polyalcoholization of the carboxy($C_{1-4}$) alkyldextran polyalcohol used for the manufacture of the drug carrier according to the present invention is not particularly limited. Preferably, dextran polyalcohols constituting the carboxy($C_{1-4}$)alkyldextran polyalcohol may be those obtained by treating a dextran under a condition which enables substantially complete polyalcoholization, which have been subjected to polyalcoholization to such an extent that they can be used for DDS compounds.

The sort of the dextran used for the preparation of the carboxy($C_{1-4}$)alkyldextran polyalcohol is not particularly limited, and the dextran may contain α-D-1,6-linkages at any rate. For example, dextran containing α-D-1,6-linkages at a rate of 85% or more, 90% or more, or 96% or more can be used. The molecular weight of the dextran is not particularly limited, and for example, (dextran having a molecular weight of from about 10,000 to about 2,000,000, preferably from about 50,000 to about 800,000 can be used. As the $C_{1-4}$ alkyl group constituting the carboxy($C_{1-4}$)alkyl group of the carboxy($C_{1-4}$)alkyldextran polyalcohol, a linear or branched $C_{1-4}$ alkyl group, specifically, methyl group, ethyl group, n-propyl group, isopropyl group, n-butyl group, sec-butyl group or the like can be used, and methyl group can preferably be used.

When dextran is used as a starting material, the dextran can be treated successively with a large excess amount of sodium periodate and sodium borohydride to obtain a dextran polyalcohol subjected to substantially complete polyalcoholization. However, the method for the polyalcoholization of dextran is not limited to the method mentioned above, and any method available to those skilled in the art may be utilized. The carboxy($C_{1-4}$)alkylation can be carried out, for example, by reacting a halogenated ($C_{1-4}$) alkylcarboxylic acid such as chloroacetic acid, bromoacetic acid, α-chloropropionic acid, α-methyl-α-chloropropionic acid, β-chloropropionic acid, α-methyl-β-chloropropionic acid, α-chlorobutyric acid, β-chlorobutyric acid, or τ-chlorobutyric acid, preferably chloroacetic acid, with hydroxyl groups of the dextran polyalcohol to achieve partial or complete carboxy($C_{1-4}$)alkylation of the hydroxyl groups.

For example, the dextran polyalcohol is dissolved in an inert solvent which does not participate in the reactions (e.g., water, N,N-dimethylformamide, or dimethyl sulfoxide), and the resulting solution is added with a halogenated ($C_{1-4}$) alkylcarboxylic acid or a salt thereof in the presence of a base (e.g., sodium hydroxide or potassium hydroxide), and then the mixture is allowed to react for several minutes to several days at a temperature under ice-cooling to about 100° C. The degree of introduction of the carboxy($C_{1-4}$)alkyl group may be easily controlled, for example, by suitably choosing the reaction temperature of the carboxy($C_{1-4}$) alkylation or the amount of the halogenated ($C_{1-4}$) alkylcarboxylic acid or bases used as reagents, and these means are well-known to those skilled in the art. The degree of the carboxy($C_{1-4}$)alkylation based on one hydroxyl group of the dextran polyalcohol is not particularly limited, and for example, the degree based on one constitutional saccharide residue may be in the range of from 0.01 to 2.0, preferably from 0.1 to 1.0. In such manners, aqueous solutions of the carboxy($C_{1-4}$)alkyldextran polyalcohol in the form of alkali metal salts such as sodium salt, potassium salt or the like can be prepared.

In addition to the polysaccharide derivatives in the form of alkali metal salts as prepared above, those in the form of organic amine salts may be used as a material for the drug carrier. The polysaccharide derivatives in the form of organic amine salts can be dissolved in an organic solvent which is substantially free from water in a high concentration, and accordingly, the use of this salt sometimes enables the reaction in a nonaqueous system and significant elevation of the reaction efficiency. As the organic amine salt, for example, salts of aliphatic amines such as triethylamine, trimethylamine, or triethanolamine; salts of alicyclic and aromatic amines such as N-methylpyrrolidine, N-methylpiperidine, N-methylmorpholine, or dimethylaminopyridine) or quaternary ammonium salts such as tetramethylammonium chloride or tetraethylammonium chloride can be used.

The conversion from the sodium salt of the polysaccharide derivative into a corresponding organic amine salt can be carried out by using an ion exchange resin or the like. For example, a sodium salt of a carboxymethyldextran polyalcohol may be dissolved in water, applied to a column charged with Bio-Rad AG50W-X2 (200–400 mesh, H⁺ type) resin, and eluted with water, and then the resulting effluent can be added with an organic amine such as triethylamine and lyophilized. Alternatively, it is also possible to carry out the conversion by one step, i.e. by dissolving a sodium salt of a carboxymethyldextran polyalcohol in water and then passing the solution through a triethylammonium type resin.

The drug complex of the present invention can be prepared, for example, by preparing a compound represented by R'—NH—Y—CH$_2$—O—CO-Q, wherein the definitions are the same as the above-mentioned, in an appropriate manner, removing the protective group if necessary, and then binding the amino group at the N-terminal of the spacer and the carboxyl group of a carboxymethyldextran polyalcohol to each other by means of an acid-amide bond. For example, a peptide compound protected at its N-terminal may be bound to the amino group of NH$_2$—Y—CH$_2$—OH via an acid-amide bond, the peptide chain may be elongated if necessary, and then a CO—X or CO-Q moiety may be introduced to the hydroxyl group. When a CO—X moiety is introduced, X may further be converted into Q. As a reactant used for the introduction of a CO—X moiety, p-nitrophenyl dicarbonate, p-nitrophenyl chloroformate (corresponds to p-nitrophenoxy group), 1,1'-carbonyldiimidazole (X corresponds to imidazoyl group) or the like can be used. For a method of introducing a CO-Q moiety, there can be used Cl—CO-Q obtained by reacting Q with phosgene, X—CO-Q (X corresponds to p-nitrophenoxy group) obtained by reacting Q with p-nitrophenyl chloroformate or the like. When R'—NH—Y—CH$_2$—O—CO—X is converted into R'—NH—Y—CH$_2$—O—CO-Q, a drug compound or a protected drug compound is reacted, and if necessary, a base such as triethylamine and diisopropylethylamine, or an activator such as 1-hydroxybenzotriazole may be added to the reaction system depending on the kinds of X and Q. Then, the protective group can be eliminated in an appropriate manner depending on the kind of the protective group to obtain the desired product. Kinds of the protective group and manners for elimination thereof are described, for example, in T. W. Green and P. G. M. Wuts, "Protective Groups in Organic Synthesis, 2nd ed.", John Wiley & Sons, Inc. (1991) and the like. For example, where t-butylcarbonyl group is used, acids such as trifluoroacetic acid, acetic acid and formic acid, preferably relatively weak acids such as formic acid can be used. Where trityl group is used, acids such as acetic acid can be used. Where 9-fluorenylmethylcarboxyl group is used, bases such as piperazine can be used.

For the formation of an acid-amide bond, dehydration condensation agents ordinarily used for synthesis of peptide chains, for example, N,N'-dicycloalkylcarbodiimides such as N,N'-dicyclohexylcarbodiimide (DCC), carbodiimide derivatives such as 1-ethyl-3-(3-dimethylaminopropyl) carbodiimide (EDAPC), benzotriazole derivatives such as 1-hydroxybenzotriazole (HOBT), 1-ethoxycarbonyl-2-ethoxy-1,2-dihydroxyquinoline (EEDQ) and the like can be used. In addition, the reaction may also be performed by the activated ester method or the acid halide method.

When the reaction using a polysaccharide derivative is performed in a non aqueous system, any organic solvents may be used so long as they are substantially free from water and can dissolve reactants (an organic amine salt of a polysaccharide derivative and H—R—NH—Y—CH$_2$—O—CO-Q in a free form or a form of salt: H—R represents that the N-terminal is not protected). For example, N,N-dimethylformamide, dimethyl sulfoxide, acetamide, N-methylpyrrolidone, sulfolane and the like can preferably be used. Although the amount of the residue of the drug compound which is introduced into the drug carrier is not particularly limited, the amount should be suitably chosen depending on the sort of the residue of a drug compound, and from the viewpoints of pharmacokinetics, efficacy, and toxicity of the drug complex. Generally, the range of approximately from 0.1 to 30% by weight, preferably approximately from 2 to 15% by weight can be chosen. The ratio of residues of the drug compound introduced to the drug carrier can be easily determined by, for example, absorption spectrometric analysis.

Further specific examples of the manufacturing method of the drug complex of the present invention will be shown in the examples. Those skilled in the art can manufacture the drug complex of the present invention that falls within the aforementioned general formula (I) on the basis of the above general explanation and the specific explanation in the examples by appropriately choosing starting materials, reagents and the like, and if necessary, by applying appropriate modifications and alterations to the reaction conditions and processes.

The drug complex of the present invention is characterized in that the complexes can specifically exhibit desired pharmacological activity at a local site such as tumorous sites or inflammatory sites depending on the sort of a residue of a drug compound (e.g., residues of drug compounds such as antineoplastic agents or antiinflammatory agents), and can reduce toxicity inherent to the drug compound, per se. For example, the drug complex having a carboxymethyldextran polyalcohol as a polysaccharide derivative moiety has excellent blood vessel permeability, and also tumor selectivity and inflammatory site selectivity.

In addition, the drug complex of the present invention has characteristic feature in that, when the spacer moiety is enzymatically hydrolyzed by a protease (peptidase), the urethane bond of aminobenzyloxycarbonylamide is immediately hydrolyzed. According to the drug complex of the present invention, the released drug compound thus contains no residual amino acid derived from the spacer, and the efficacy of the drug compound, per se, will not be reduced. Furthermore, the drug complex of the present invention is characterized in that an appropriate releasing rate of the drug compound can be obtained by choosing the type of the spacer A medicament comprising the drug complex of the present invention may generally be filled in vials or the like in the form of a lyophilized product or the like, and provided for clinical use as preparations for parenteral administration such as injections or drip infusions which are dissolved upon use. However, the form of pharmaceutical preparations of the medicament is not limited to the aforementioned forms. For the manufacture of the aforementioned pharmaceutical preparations, pharmaceutical additives available in the field of the art, for example, solubilizers, pH modifiers, stabilizers and the like can be used. Although the dose of the above medicament is not particularly limited, the dose should normally be decided in view of the dose of the drug compound that constitutes the residue of the drug compound, the amount of the residue of the drug compound introduced into the drug complex, the condition of a patient, the sort of a disease and the like. For example, where a drug complex introduced with about 6% by weight of the residue of the antineoplastic agent mentioned in claim 2 of Japanese Patent Unexamined Publication (KOKAI) No. (Hei) 6-87746/1994 is parenterally administered, about 0.1 to 100 mg, preferably about 1 to 30 mg per $m^2$ of body surface area per day may generally be administered once a day, and the administration may preferably repeated every 3 to 4 weeks.

A compound of the present invention provided from another aspect is represented by the following general formula (II): R'—NH—Y—CH$_2$—O—CO-Q, wherein R' is a group comprising one amino acid or peptide-bonded 2 to 8 amino acids of which the N-terminal is protected or not protected; Y is phenylene group which may be substituted; and Q is a residue of a drug compound. In this compound, preferred are those wherein Y is unsubstituted p-phenylene group, R' is a group represented by H-Gly-Gly-Phe-Gly- (SEQ ID NO: 1) or H-Gly-Gly-Gly-Phe- (SEQ ID NO: 2), and the drug compound is (1S,9S)-1-amino-9-ethyl-5-fluoro-2,3-dihydro-9-hydroxy-4-methyl-1H,12H-benzo[de]pyrano[3',4':6,7]indolizino[1,2-b]quinoline-10,13-(9H, 15H)-dione.

In addition, the present invention also provides a compound represented by the following general formula (III): A-R—NH—Y—CH$_2$—O—CO—X, wherein A is a polymer as a drug carrier; R is a spacer, wherein said spacer is an amino acid or an oligopeptide comprising 2 to 8 amino acids; Y is phenylene group which may be substituted; X is selected from the group comprising hydroxyl group, —O-M wherein M is a protective group for carboxyl group, or an eliminating group. Kinds of the protective group for carboxyl group are not particularly limited, and any protective group may be used so long as it is available to those skilled in the art. In addition, any eliminating group may be used so long as it functions as an eliminating group in the substitution on the carbonyl carbon, and examples include halogen atoms such as chlorine atom and bromine atom, alkoxyl groups such as ethoxy group, and arylsulfonyloxy groups such as p-toluenesulfonyloxy group and the like. Symbols such as Y, Q and R in the formulas (II) and (III) have the same meanings as those described above for the formula a). These compounds represented by the formulas (II) and (III) are useful as synthetic intermediates for the manufacture of the drug complex of the present invention.

EXAMPLES

The present invention will be explained more specifically by way of examples; however, the scope of the present invention is not limited to the following examples.

In the examples, the carboxymethylation degree (degree of substitution with carboxymethyl groups per saccharide residue as a building unit) was determined by converting the sodium salt of the carboxymethyldextran polyalcohol into free acid form, and then dissolving the free acid in 0.1 N aqueous sodium hydroxide and titrating the solution with 0.1 N hydrochloric acid. An aqueous solution of the sodium salt of the carboxymethyldextran polyalcohol was applied to a Bio-Rad AG50W-x2 ($H^+$) column, and the passed solution was lyophilized and used as a sample. The sample was dissolved in a given excess amount of 0.1 N aqueous sodium hydroxide, and titrated with 0.1 N hydrochloric acid by using phenolphthalein as an indicator. The carboxymethylation degree was determined in accordance with the equation; $13.4(a \cdot b)/[s-5.8(a \cdot b)]$ wherein symbol "s" represents the amount of the collected sample (mg), symbol "a" represents the given excess amount of 0.1 N aqueous sodium hydroxide (ml), and symbol "b" represents the amount of 0.1 N A hydrochloric acid required for the titration (ml). The amount of the introduced drug (% by weight) was calculated from the results of absorption spectrometry (around 362 nm) utilizing the characteristic absorption of the drug. The gel filtration was performed under the following conditions: column; TSK gel G4000 FW$_{XL}$, eluate: 0.1 M NaCl, flow rate; 0.8 ml/min, and column temperature; 40° C.

DX-8951 represents a drug compound: (1S,9S)-1-amino-9-ethyl-5-fluoro-2,3-dihydro-9-hydroxy-4-methyl-1H,12H-benzo[de]pyrano[3',4':6,7]indolizino[1,2-b]quinoline-10, 13-(9H,15H)-dione which was disclosed in claim 2 of Japanese Patent Unexamined Publication (KOKAI) (Hei) No. 6-87746/1994, and —CO-DX-8951 represents that the amino group at the 1-position of the drug compound forms a peptide bond with the carbonyl group represented by —CO—. It should be understood that DX-8951 has a lactone ring which exists in the ring-closed or ring-opened form, or in the form of the mixture thereof. The building units of the saccharide chain shown in the following schemes are introduced with one or two carboxymethyl groups. It should be noted that this building units are shown as an example of the building unit of the saccharide chain, and that the drug carrier moiety of the drug complex of the present invention is not formed by the repetition of the above building unit. The compound numbers in the examples correspond to those in the following schemes. For example, Compound 2a in Example 5 corresponds to Compound 2a in the scheme, which represents a compound in which the peptide moiety of the formula in the scheme is GGFG (SEQ ID NO: 1) (In the scheme, this is shown as Peptide= GGFG.).

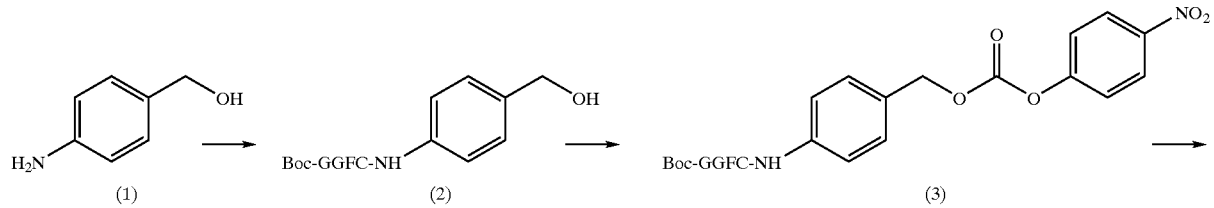

13
14
-continued
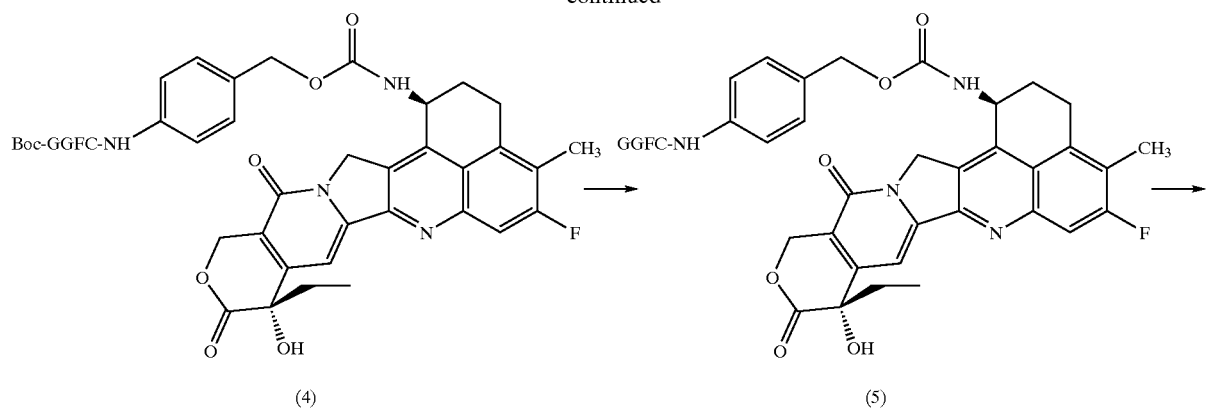
(4) (5)
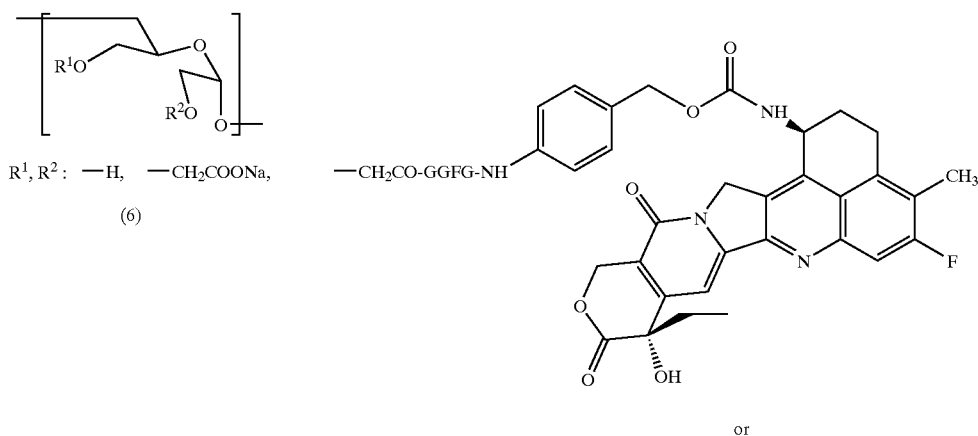
(6)
Boc = (CH₃)₃COCO—
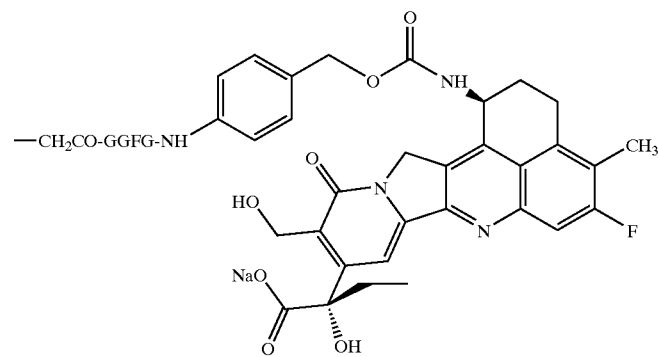
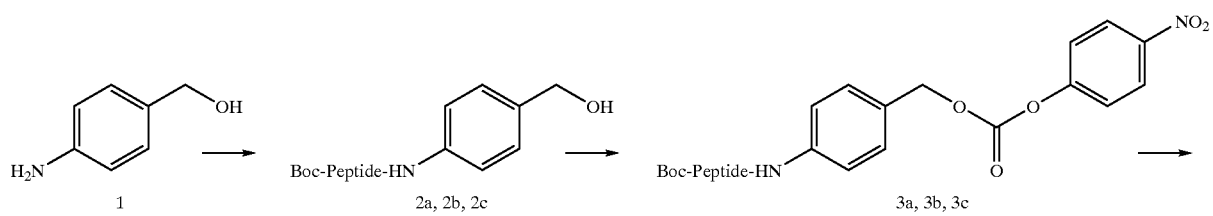

-continued
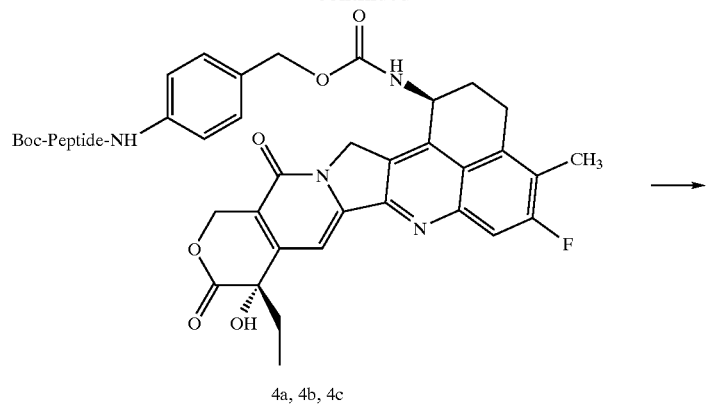
4a, 4b, 4c
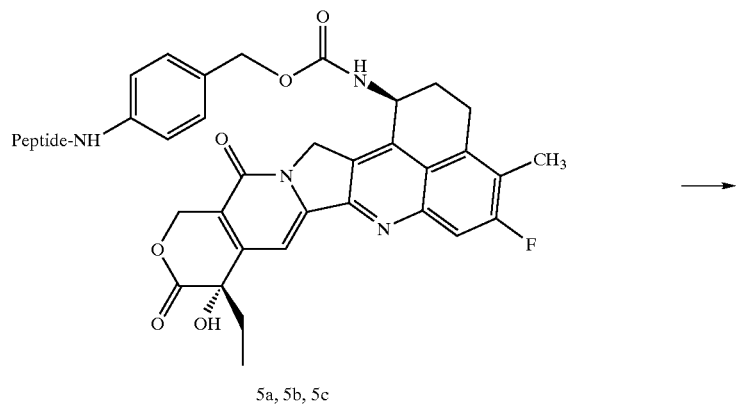
5a, 5b, 5c
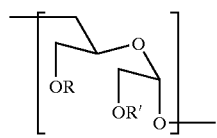
6a, 6b, 6c
R, R'=H, CH$_2$COONa,
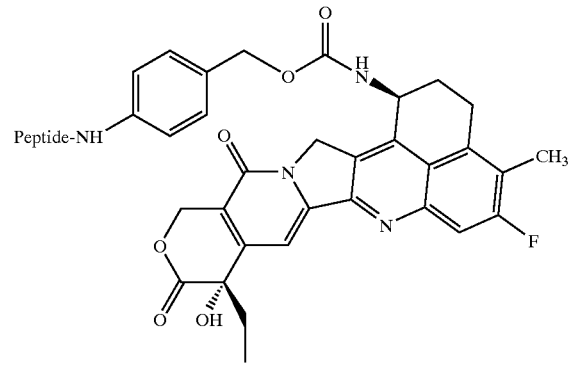
or
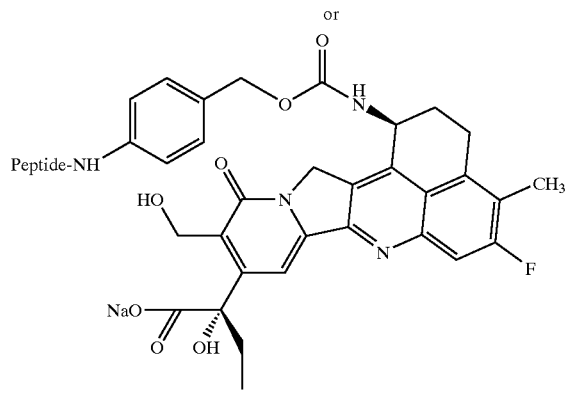
a: Peptide = GGFG (SEQ ID NO : 1)
b: Peptide = GGGF (SEQ ID NO : 2)
c: Peptide = GG

Example 1

Synthesis of Carboxymethyldextran polyalcohol-Gly-Gly-Phe-Gly-NH-p-C$_6$H$_4$—CH$_2$—O—CO-DX-8951. (SEQ ID NO: 1)

Dextran T500 (20 g, Pharmacia, molecular weight: 500K) was dissolved in 0.1 M acetic buffer (pH 5.5, 2,000 ml), and added with an aqueous solution (2,000 ml) of sodium periodate (66.0 g). The mixture was stirred at 4° C. for 10 days with shielding from the light. Then, the mixture was added with ethylene glycol (14.0 ml) and stirred overnight. The reaction mixture was adjusted to pH 7 with $ M aqueous sodium hydroxide. Sodium borohydride (28 g) was added to the mature and dissolved, and then the mixture was stirred overnight. The reaction mixture was adjusted to pH 5.5 with acetic acid under ice cooling, and stirred at 4° C. for 1 hour. The mixture was adjusted to pH 7.5 with 8 M aqueous sodium hydroxide. The resulting aqueous solution was desalted by ultrafiltration using a Biomax-50 membrane. The residual solution, which did not pass through the membrane, was lyophilized to obtain dextran polyalcohol (10.5 g). The molecular weight (gel filtration, pullulan standard) of the resulting product was 159K.

The resulting dextran polyalcohol (7.5 g) was added to an aqueous solution obtained by dissolving sodium hydroxide (31.5 g) in water (225 ml), and dissolved at room temperature. Monochloroacetic acid (45 g) was added to the solution under ice cooling and dissolved, and the mixture was allowed to react at room temperature overnight. The reaction mixture was adjusted to pH 8 with acetic acid, and desalted by ultrafiltration using a Biomax-50 membrane. The residual solution, which did not pass through the membrane, was lyophilized to obtain sodium salt of carboxymethyldextran polyalcohol (8.5 g). The molecular weight (gel filtration, pullulan standard) of the resulting product was 274K, and the carboxymethylation degree thereof was 0.4.

1-Ethoxycarbonyl-2-ethoxy-1,2-dihydroxyquinoline (989 mg) was added to a mixture of Boc-Gly-Gly-Phe-Gly-OH (SEQ ID NO: 1) (875 mg), 4-aminobenzyl alcohol (492 mg) and N,N-dimethylformamide (10 ml). The resulting mixture was allowed to react with stirring at room temperature overnight, and then the reaction mixture was evaporated to dryness under reduced pressure. The residue was purified by silica gel column chromatography (eluate: a solution of dichloromethane:methanol=96:4) to obtain 800 mg of Compound (2).

$^1$H-NMR (DMSO-d$_6$)δ: 9.73 (s, 1H), 8.38 (s, 1H), 8.17 (d, 1H, J=7.2 Hz), 7.91–7.93 (m, 1H), 7.56 (d, 2H, J=8.0 Hz), 7.24–7.26 (m, 4H), 7.24 (d, 2H, J=8.0 Hz), 7.17–7.20 (m, 1H), 4.50–4.54 (m, 1H), 4.44 (s, 2H), 3.66–3.94 (m, 3H), 3.63 (dd, 1H, J=4.8, 16.7 Hz), 3.56 (d, 2H, J=5.6 Hz), 3.09 (dd, 1H, J=4.8, 13.5 Hz), 2.83 (dd, 1H, J=9.6, 13.5 Hz), 1.38 (s, 9H).

A mixture of Compound (2) (466 mg), bis(4-nitrophenyl) carbonate (522 mg), diisopropylethylamine (0.224 ml), 4-(dimethylamino)pyridine (10.5 mg) and tetrahydrofuran (3 ml) was allowed to react with stirring at room temperature for 4 days. Then, the reaction mixture was evaporated to dryness under reduce pressure. The residue was purified by silica gel column chromatography (eluate: a solution of dichloromethane:methanol=99:1) to obtain 206 m, of Compound (3).

$^1$H-NMR (DMSO-d$_6$)δ: 9.88 (s, 1H), 8.40–8.42 (m, 1H), 3.31 (d, 2H, J=9.5 Hz), 8.27–8.28 (m, 1H), 7.92–7.94 (m, 1H), 7.67 (d, 2H, J=7.9 Hz), 7.55 (d, 2H, J=9.5 Hz), 7.41 (d, 2H, J=7.9 Hz), 7.24–7.26 (m, 4H), 7.17–7.20 (m, 1H), 6.93–6.95 (m, 1H), 5.25 (s, 1H), 4.50–4.53 (m, 1H), 3.77–3.95 (m, 3H), 3.61–3.66 (m, 1H), 3.55–3.57 (m, 2H), 3.08 (dd, 1H, J=4.8, 13.5 Hz), 2.83 (dd, 1H, J=9.5, 13.5 Hz), 1.38 (s, 9H).

A mixture of Compound (3) (185 mg), methanesulfonate of DX-8951 (152 mg), 1-hydroxybenzotriazole (54 mg), diisopropylethylamine (0.093 ml) and N,N-dimethylformamide (20 ml) was allowed to react with stirring at room temperature for 2 days. Then, the reaction mixture was evaporated to dryness under reduced pressure. The residue was purified by silica gel column chromatography (eluate: a solution of dichloromethane methanol=96:4). The resulting yellow solid was further purified by silica gel column chromatography (eluate: a solution of dichloromethane:methanol=97:3 containing 0.5% acetic acid) to obtain 130 mg of Compound (4).

$^1$H-NMR (DMSO-d$_6$) δ: 9.84 (s, 1H), 8.40–8.41 (m, 1H), 8.19 (d, 1H, J=8.0 Hz), 8.04 (d, 1H, J=8.8 Hz), 7.92–7.93 (m, 1H), 7.74 (d, 1H, J=11.1 Hz), 7.63 (d, 2H, J=8.01 Hz), 7.37 (d, 2H, J=8.0 Hz), 7.32 (s, 1H), 7.24–7.26 (m, 4H), 7.16–7.20 (m, 1H), 6.94–6.95 (m, 1H), 6.48 (s, 1H), 5.46 (d, 1H, J=16.7 Hz), 5.41 (d, 1H, J=16.7 Hz), 5.24–5.34 (m, 3H), 5.08 (s, 2H), 4.49–4.52 (m, 1H), 3.92 (dd, 1H, J=5.6, 16.7 Hz), 3.85 (dd, 1H, J=5.6, 16.7 Hz), 3.78 (dd, 1H, J=5.6, 16.7 Hz), 3.63 (dd, 1H, J=4.8, 16.7 Hz), 3.54–3.56 (m, 1H), 3.31–3.33 (m, 2H), 3.08 (dd, 1H, J=4.8, 13.5 Hz), 2.83 (dd, 1H, J=10.3, 13.5 Hz), 2.38 (s, 3H), 1.86–1.89 (m, 2H), 1.37 (s, 9H), 0.88 (t, 3H, J=7.2 Hz) Mass (FAB); m/e 797 (M+1)

Compound (4) (98 mg) was dissolved in trifluoroacetic acid (1.5 ml) and allowed to stand for 1.5 hours. The reaction mixture was added dropwise to ether (30 ml), and the precipitate was collected by filtration and washed with ether to obtain 100 mg of Compound (5).

$^1$H-NMR (DMSO-d$_6$)δ: 9.86 (s, 1H), 8.48–8.61 (m, 2H), 8.37 (d, 1H, J=8.3 Hz), 8.00–8.20 (m, 1H), 7.75 (d, 1H, J=10.7 Hz), 7.66 (d, 2H, J=8.8 Hz), 7.41 (d, 2H, J=8.8 Hz), 7.37 (s, 1H), 7.24–7.27 (m, 4H), 7.17–7.19 (m, 1H), 6.48 (s, 1H), 5.72 (d, 1H, J=19.0 Hz), 5.33–5.48 (m, 3H), 5.23–5.30 (m, 1H), 5.08–5.11 (m, 2H), 4.58–4.61 (m, 1H), 3.84–3.99 (m, 3H), 3.71 (dd, 1H, J=4.9, 16.6 Hz), 3.56–3.66 (m, 2H), 3.22–3.30 (m, 1H), 3.12–3.18 (m, 1H), 3.09–3.11 (m, 1H), 2.78–2.83 (m, 1H), 2.46–2.57 (m, 1H), 2.38 (s, 3H), 2.18–2.23 (m, 1H), 1.82–1.93 (m, 2H), 0.90 (t, 3H, J=7.3 Hz)

Figure 2:
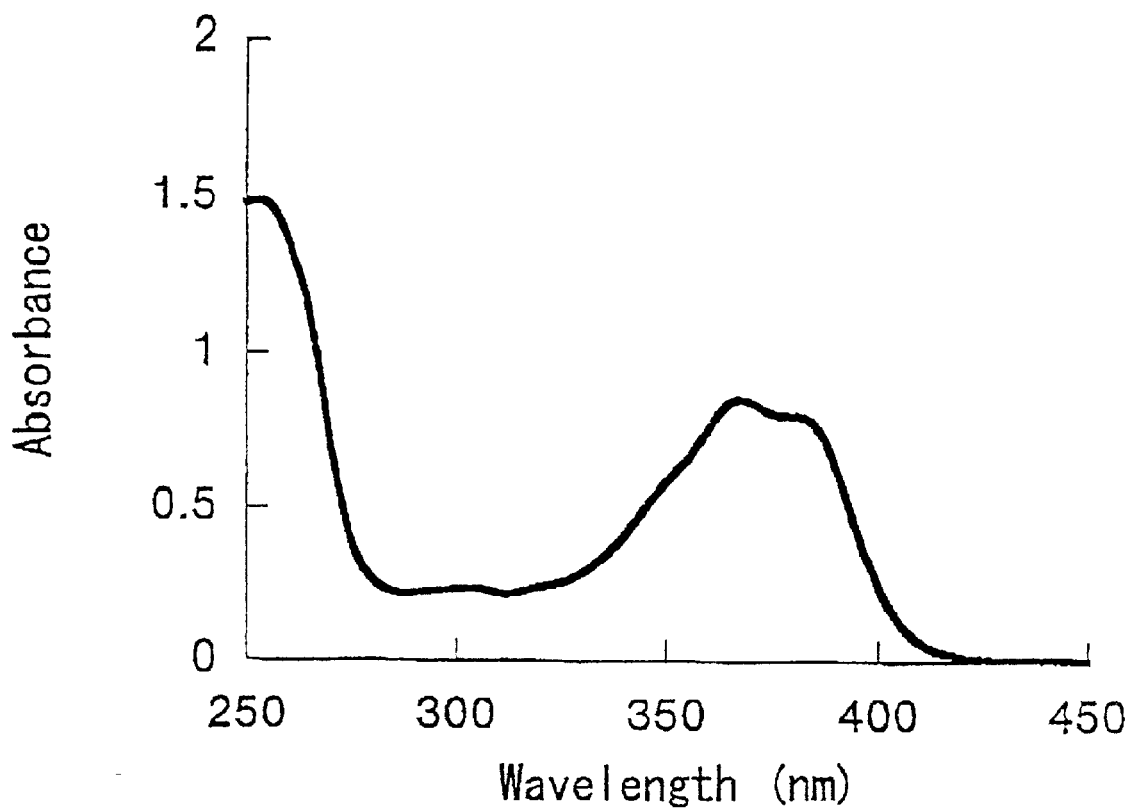
FIG. 2 shows an ultraviolet absorption spectrum of the drug complex of the present invention (Example 1).

Compound (5) (95 mg) was dissolved in water (5 ml) and methanol (10 ml). The solution was added to a solution obtained by dissolving the sodium salt of carboxymethyl-dextran polyalcohol obtained above (600 mg) in water (10 ml) and methanol (20 ml). The resulting mixture was added with water-soluble carbodiimide (26 mg) and 1-hydroxybenzotriazole (15 mg), and then adjusted to pH 7.0 with 0.1 N aqueous sodium hydroxide. The mixture was stirred at room temperature for 2 hours, then added with water-soluble carbodiimide (13 mg), and allowed to react at room temperature overnight. Water (500 ml) was added to the reaction mixture and subjected to ultrafiltration using an ultrafiltration membrane 10K (Filtron Co.). The residual solution, which did not pass through the membrane, was adjusted to pH 9 with 0.1 N aqueous sodium hydroxide and passed through a filtration membrane (0.16 μm, Filtron Co.). The passed solution was desalted by ultrafiltration using a Biomax-50 membrane. The residual solution, which did not pass through the membrane, was filtered through a Millipore filter (0.22 μm), and lyophilized to obtain 490 mg of Compound (6). This compound was dissolved in 0.1 M aqueous sodium chloride, and analyzed by GPC (column: TOSOH TSX Gel PW-4000XL, solvent: 0.1 M NaCl, flow rate: 0.8 ml/min). The results of the GPC analysis and an ultraviolet absorption spectrum (0.1 M Tris buffer, pH 10.0, 0.20 mg/ml) of the compound are shown in FIGS. 1 and 2, respectively. The content of the drug compound residue in the compound was found as 2.3% (w/w) by quantitative analysis based on absorption spectrophotometry at 366 nm in 0.1 M Tris buffer (pH 10.0):acetonitrile=7:3.

Example 2

Release of the Drug Compound From the Drug Complex

The drug complex obtained in Example 1 was dissolved in a Meth A (murine fibrosarcoma Meth A) homogenate or a buffer at 37° C. (378 μg/ml). After 20 hours, released DX-8951 was determined. The compound wherein the spacer and DX-8951 were bound to each other without p-aminobenzyloxycarbonyl group was prepared and used as a comparative compound. The result is shown in Table 1. The released amount of the drug is expressed in percentage of the released amount of the drug to the amount of the drug in the drug complex used. The drug complex of the present invention was rapidly released in the weakly acidic homogenate, but hardly released in the buffer. On the other hand, the comparative compound was released in a slight amount in the weakly acidic homogenate, but not released in the buffer.

TABLE 1

| Reaction system | Compound in Example 1 | Comparative compound |
|---|---|---|
| Meth A homogenate (pH 4.5) | 37.7 | 0.106 |
| Meth A homogenate (pH 5.5) | 38.1 | 0.034 |
| Meth A homogenate (pH 6.5) | 4.25 | 0.000 |
| Buffer (pH 4.5) | 0.190 | 0.000 |
| Buffer (pH 5.5) | 0.178 | 0.000 |
| Buffer (pH 6.5) | 0.171 | 0.000 |
| Buffer (pH 7.5) | 0.138 | — |
| Mouse plasma | 0.186 | — |

—: No examination

Example 3

Maximum Tolerated Dose (MTD) of the Drug Complex of Example 1 to Meth A Tumor-Bearing Mice Meth A cells were transplanted into BALB/c mice to prepare Meth A tumor-bearing mice. On the 20th day, single administration of the drug complex of Example 1 was carried out. After the administration, measurement of the body weight and observation of toxic death were made with time and the maximum body-weight reduction rate and mortality were calculated, which are shown in Table 2. The dose is expressed in terms of the weight of anhydrous free base of DX-8951. Slight reduction of the body weight was observed in administration of 2.5 mg/kg, and toxic death of all the cases was observed in administration of 10 mg/kg, and accordingly, MTD of Example 1 was determined as 5 to 7.5 mg/kg.

TABLE 2

| Compound | Dose (mg/kg) | BWLmax[a] (%)[day] | N[b] |
|---|---|---|---|
| Control | 0 | <0 | 0/2 |
| Example 1 | 30 | 17.9[22] | 2/2 |
| | 10 | 32.8[26] | 2/2 |
| | 2.5 | 2.2[22] | 0/2 |
| | 0.625 | <0 | 0/2 |
| | 0.156 | <0 | 0/2 |

[a]The maximum body-weight reduction rate (The numbers in the parentheses are the days when the maximum reduction was observed.)
<0 means that reduction of the body weight was not observed.
[b]Mice died/mice used

Example 4

Antineoplastic Activity of the Drug Complex of Example 1

Meth A cells (murine fibrosarcoma Meth A) were transplanted into BALB/c mice to prepare Meth A tumor-bearing mice. On the 7th day after the transplantation, the drug complex of Example 1 was administered. The weight of the tumor was measured on the 21th day to evaluate the inhibitory activity on the tumor and the toxicity. The results are shown in Table 3. In the table, * represents significance in Dunnet's test (* $P<0.001$,  $P<0.01$), the dose is expressed in terms of the weight of anhydrous free base of DX-8951, and IR represents the diminution rate of the tumor. The drug complex of Example 1 apparently diminished tumor weight dose-dependently.

TABLE 3

| Compound | Dose (mg/kg) | Average tumor weight (g) | IR(%) | BWLmax[a] (%)[day] | N[b] |
|---|---|---|---|---|---|
| Control | 0 | 2.315 ± 0.366 | 0 | <0 | 0/6 |
| Example 1 (the present invention) | 7.5 | 0.008 ± 0.002*** | 100 | 24.8[15] | 2/6 |
| | 5 | 0.019 ± 0.004*** | 99 | 2.9[13] | 0/6 |
| | 2.5 | 0.061 ± 0.016*** | 97 | <0 | 0/6 |
| | 1.25 | 0.610 ± 0.180*** | 74 | 0.3[8] | 0/6 |
| | 0.625 | 1.247 ± 0.280** | 46 | <0 | 0/6 |

[a]The maximum body-weight reduction rate (The numbers in the parentheses are the days when the maximum reduction was observed.)
[b]Mice died/mice used

Example 5

Synthesis of Carboxymethyldextran polyalcohol-Gly-Gly-Phe-Gly-NH-p-C $_6$H$_4$—CH$_2$—O—CO-DX-8951 (SEQ ID NO: 1) Using Formic Acid as a Deprotecting Agent Dextran T500 (20 g, Pharmacia, molecular weight: 500K) was dissolved in 0.1 M acetic buffer (pH 5.5, 2,000 ml), and added with an aqueous solution (2,000 ml) of sodium periodate (66.0 g). The mixture was stirred at 4° C. for 10 days with shielding from the light. Then, the mixture was added with ethylene glycol (14.0 ml) and stirred overnight. The reaction mixture was adjusted to pH 7 with 8 M aqueous sodium hydroxide. Sodium borohydride (28 g) was added to the mixture and dissolved, and then the mixture was stirred overnight. The reaction mixture was adjusted to pH 5.5 with acetic acid under ice cooling, and stirred at 4° C. for 1 hour. The mixture was adjusted to pH 7.5 with 8 M aqueous sodium hydroxide. The resulting aqueous solution was desalted by ultrafiltration using a Biomax-50 membrane.

The residual solution, which did not pass through the membrane, was lyophilized to obtain dextran polyalcohol (10.5 g). The molecular weight (gel filtration, pullulan standard) of the resulting product was 159K.

The resulting dextran polyalcohol (7.5 g) was added to an aqueous solution obtained by dissolving sodium hydroxide (31.5 g) in water (225 ml), and dissolved at room temperature. Monochloroacetic acid (45 g) was added to the solution under ice cooling and dissolved, and the mixture was allowed to react at room temperature overnight. The reaction mixture was adjusted to pH 8 with acetic acid, and desalted by ultrafiltration using a Biomax-50 membrane. The residual solution, which did not pass through the membrane, was lyophilized to obtain sodium salt of carboxymethyldextran polyalcohol (8.5 g). The molecular weight (gel filtration, pullulan standard) of the resulting product was 274K, and the carboxymethylation degree thereof was 0.4.

1-Ethoxycarbonyl-2-ethoxy-1,2-dihydroxyquinoline (989 mg) was added to a mixture of Boc-Gly-Gly-Phe-Gly-OH (SEQ ID NO: 1) (875 mg), 4-aminobenzyl alcohol (492 mg) and N,N-dimethylformamide (10 ml). The resulting mixture was allowed to react with stirring at room temperature overnight, and then the reaction mixture was evaporated to dryness under reduced pressure. The residue was purified by silica gel column chromatography (eluate: a solution of dichloromethane:methanol=96:4) to obtain 800 mg of Compound 2a.

$^1$H-NMR (DMSO-$d_6$)δ: 9.73 (s, 1H), 8.38 (s, 1H), 8.17 (d, 1H, J=7.2 Hz), 7.91–7.93 (m, 1H), 7.56 (d, 2H, J=8.0 Hz), 7.24–7.26 (m, 4H), 7.24 (d, 2H, J=8.0 Hz), 7.17–7.20 (m, 1H), 4.50–4.54 (m, 1H), 4.44 (s, 2H), 3.66–3.94 (m, 3H), 3.63 (dd, 1H, J=4.8, 16.7 Hz), 3.56 (d, 2H, J=5.6 Hz), 3.09 (dd, 1H, J=4.8, 13.5 Hz), 2.83 (dd, 1H, J=9.6, 13.5 Hz), 1.38 (s, 9H).

A mixture of Compound 2a (465 mg), bis(4-nitrophenyl) carbonate (522 mg), diisopropylethylamine (0.224 ml), 4.(dimethylamino)pyridine (10.5 mg) and tetrahydrofuran (3 ml) was allowed to react with stirring at room temperature for 4 days. Then, the reaction mixture was evaporated to dryness under reduced pressure. The residue was purified by silica gel column chromatography (eluate; a solution of dichloromethane:methanol=99:1) to obtain 205 mg of Compound 3a.

$^1$H-NMR (DMSO-$d_6$): 9.88 (a, 1H), 8.40–8.42 (m, 1H), 8.31 (d, 2H, J=9.5 Hz), 8.27–8.28 (m, 1H), 7.92–7.94 (m, 1H), 7.67 (d, 2H, J=7.9 Hz), 7.55 (d, 2H, J=9.6 Hz), 7.41 (d, 2H, J=7.9 Hz), 7.24–7.26 (m, 4H), 7.17–7.20 (m, 1H), 6.93–6.95 (m, 1H), 5.25 (s, 1H), 4.50–4.53 (m, 1H), 3.77–3.95 (m, 3H), 3.61–3.66 (m, 1H), 3.55–3.57 (m, 2H), 3.08 (dd, 1H, J=4.8, 13.5 Hz), 2.83 (dd, 1, J=9.5, 13.5 Hz), 1.38 (s, 9H).

A mixture of Compound 3a (185 mg), methanesulfonate of DX-8951 (152 mg), 1-hydroxybenzotriazole (54 mg), diisopropylethylamine (0.093 ml) and N,N-dimethylformamide (20 ml) was allowed to react with stirring at room temperature for 2 days. Then, the reaction mixture was evaporated to dryness under reduced pressure. The residue was purified by silica get column chromatography (eluate: a solution of dichloromethane:methanol=96:4). The resulting yellow solid was further purified by silica gel column chromatography (eluate: a solution of dichloromethane:methanol=97.3 containing 0.5% acetic acid) to obtain 130 mg of Compound 4a.

$^1$H-NMR (DMSO-$d_6$)δ: 9.84 (s, 1H), 8.40–8.41 (m, 1H), 8.19 (d, 1H, J=8.0 Hz), 8.04 (d, 1H, J=8.8 Hz), 7.92–7.93 (m, 1H), 7.74 (d, 1H, J=11.1 Hz), 7.63 (d, 2H, J=8.0 Hz), 7.37 (d, 2H), J=8.0 Hz), 7.32 (s, 1H), 7.24–7.26 (m, 4H), 7.16–7.20 (m, 1H), 6.94–6.95 (m, 1H), 6.48 (s, 1H), 5.46 (d, 1H, J=16.7 Hz), 5.41 (d, 1H, J=16.7 Hz), 5.24–5.34 (m, 3H), 5.08 (s, 2H), 4.49–4.52 (m, 1H). 3.92 (dd, 1H, J=5.6, 16.7 Hz) 3.85 (dd, 1H, J=5.6, 16.7 Hz), 3.78 (dd, 1H, J=5.6, 16.7 Hz), 3.63 (dd, 1H, J=4.8, 16.7 Hz), 3.54–3.56 (m, 1H), 3.31–3.33 (m, 2H), 3.08 (dd, 1H, J=4.8, 13.6 Hz), 2.83 (dd, 1H, J=10.3, 13.5 Hz), 2.38 (s, 3H), 1.86–1.89(m, 2H), 1.37 (s, 9H), 0.88 (t, 3H, J=7.2 Hz).

Compound 4a (200 mg) was dissolved in formic acid (4 ml) and allowed to stand for 2 hours. The reaction mixture was added dropwise to ether (40 Ml). The precipitate was washed with ether to obtain 198 mg of Compound 5a.

$^1$H-NMR (DMSO-$d_6$)δ: 9.90 (s, 1H), 8.48–8.50 (m, 1H), 8.33–8.36 (m, 1H), 8.27–8.30 (m, 2H), 8.00–8.08 (m, 1H), 7.74–7.76 (m, 1H), 7.63 (d, 1H, J=8.2 Hz), 7.31–7.39 (m, 3H), 7.21–7.25 (m, 5H), 7.15–7.20 (m, 1H), 5.43–5.48 (m, 2H), 5.22–5.33 (m, 3H), 6.8 (s, 2H), 4.51–4.53 (m, 1H), 3.93 (dd, 1H, J=5.5, 16.5 Hz), 3.80–3.90 (m, 2H), 3.64–3.72 (m, 3H), 3.20–3.25 (m, 1H), 3.09–3.13 (m, 1H), 3.07 (dd, 1H, J=4.1, 13.8 Hz), 2.81 (dd, 1H, J=10.1, 13.8 Hz), 2.37 (s, 3H), 2.15–2.22 (m, 2H), 1.82–1.88 (m, 2H), 0.88 (t, 3H, J=7.3 Hz).

Figure 3:
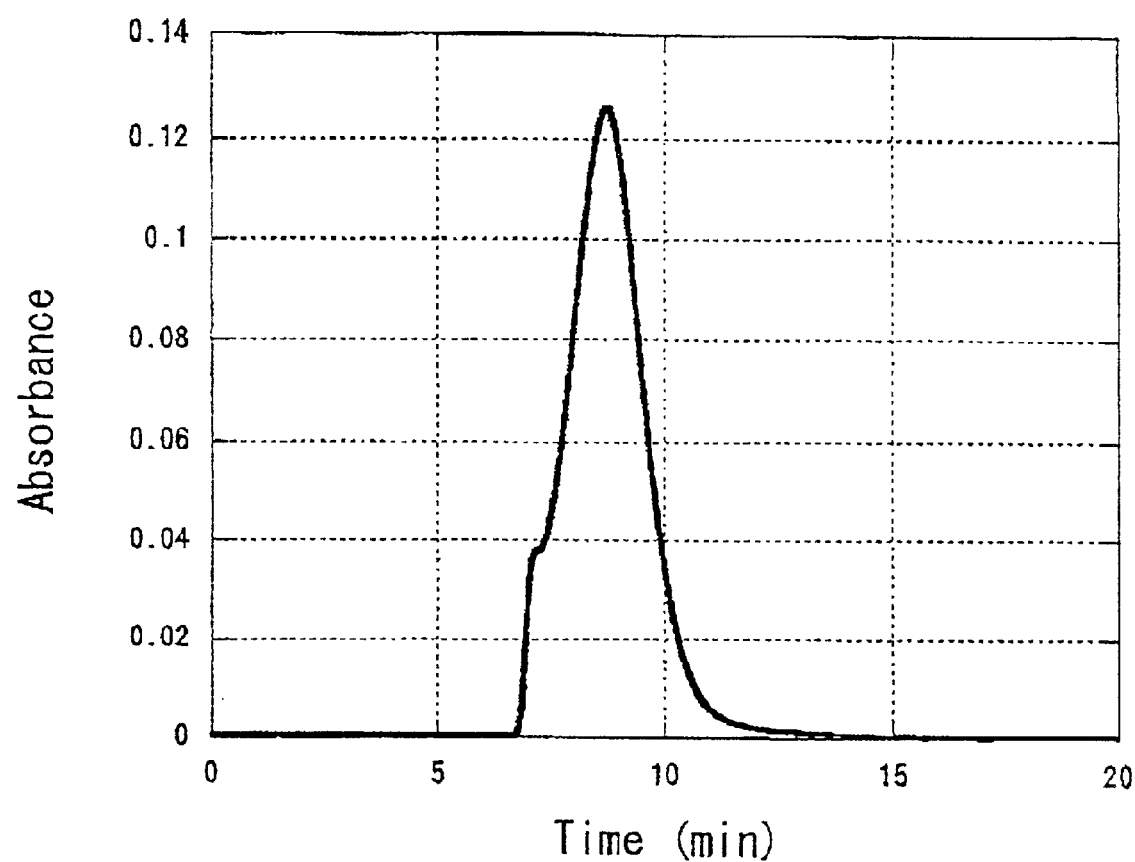
FIG. 3 shows a GPC chart of the drug complex of the present invention (Example 5).
Figure 4:
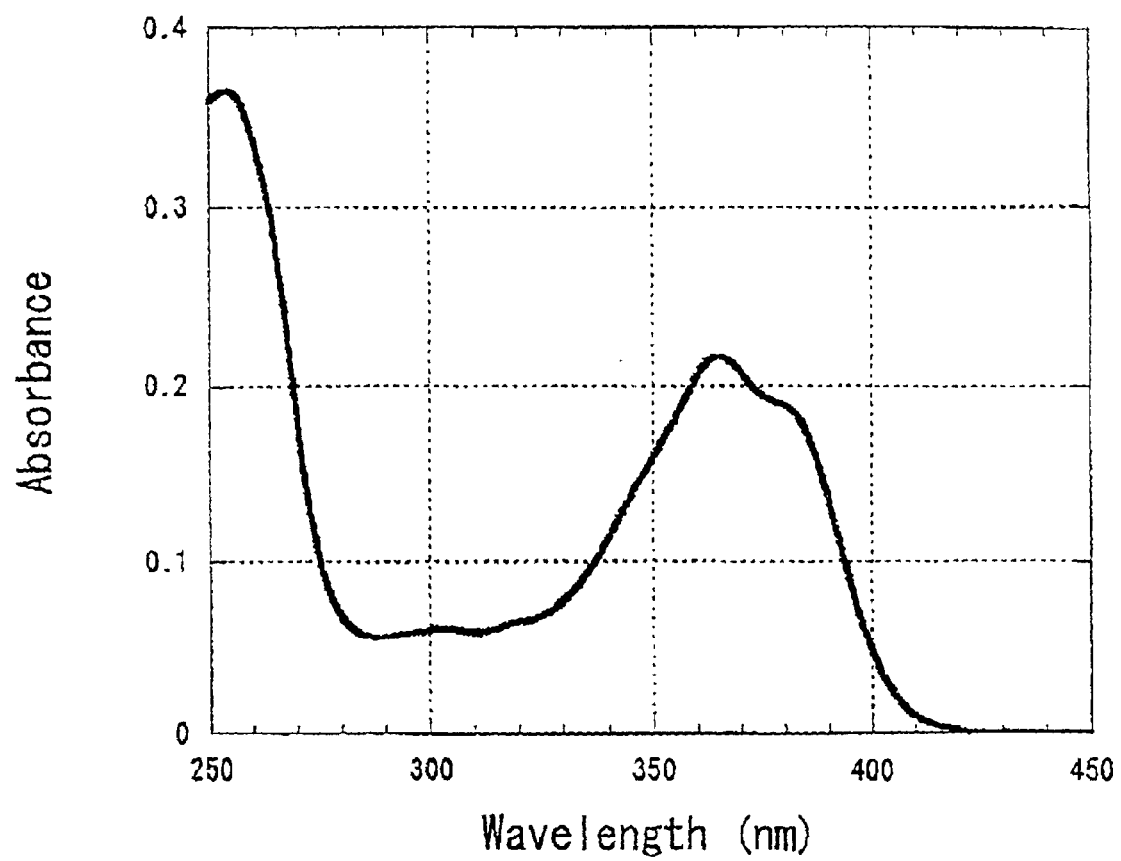
FIG. 4 shows an ultraviolet absorption spectrum of the drug complex of the present invention (Example 6).

Compound 5a (190 mg) was dissolved in water (5 ml) and methanol (10 ml). The solution was added to a solution obtained by dissolving the sodium salt of carboxymethyl-dextran polyalcohol obtained in Example 1 (1.0 g) in water (10 ml) and methanol (5 ml). The resulting mixture was added with 1-hydroxybenzotriazole (44 mg) and 1-ethyl-3-(3-dimethylaminopropyl)carbodiimide (39 mg), and then adjusted to pH 7.0 with 0.1 N aqueous sodium hydroxide. The mixture was stirred at room temperature for 3 hours, then added with 1-ethyl-3-(3-dimethylaminopropyl) carbodiimide (22 mg). The mixture was stirred at room temperature for 1.75 hours, then added with 1-ethyl-3-(3-dimethylaminopropyl)carbodiimide (11 mg), and allowed to react at room temperature overnight. The reaction mixture was adjusted to pH 8.9 with 0.1N aqueous sodium hydroxide, and then desalted by ultrafiltration using a Biomax-50 membrane. The residual solution, which did not pass through the membrane, was filtered through a Millipore filter (0.22 μm), and lyophilized. The resulting amorphous was purified with Sep-Pak $C_{18}$ cartridge (Waters Co.) and a Bio-Rad AG50W-X8 ($Na^+$ form) column, and further desalted by ultrafiltration using a Biomax-50 membrane. The residual solution, which did not pass through the membrane, was filtered through a Millipore filter (0.22 μm), and lyophilized to obtain Compound 6a (700 mg). This compound was dissolved in 0.1 M aqueous sodium chloride, and analyzed by GPC (column TOSOH TSX Gel PW-4000XL, solvent: 0.1 M aqueous NaCl containing 20% acetonitrile, flow rate: 0.8 ml/min). The results of the GPC analysis and an ultraviolet absorption spectrum (0.1 M Tris buffer, pH9.0, 0.10 mg/ml) of the compound are shown in FIGS. 3 and 4, respectively. The content of the drug compound residue in the compound was found as 3.3% (w/w) by quantitative analysis based on absorption spectrophotometry at 366 nm in 0.1 M Tris buffer (pH 10.0):acetonitrile=7:3.

Example 6

Synthesis of Carboxymethyldextran polyalcohol-Gly-Gly-Gly-Phe-NH-p-$C_6H_4$—$CH_2$—O—CO-DX-8951 (SEQ ID NO: 2) Using Formic Acid as a Deprotecting Agent Dextran T500 (20 g, Pharmacia, molecular weight: 500K) was dissolved in 0.1 M acetic buffer (pH 5.5, 2,000 ml), and added with an aqueous solution (2,000 ml) of sodium periodate (66.0 g). The mixture was stirred at 4° C. for 10 days with shielding from the light. Then, the mixture was added with ethylene glycol (14.0 ml) and stirred overnight. The reaction mixture was adjusted to pH 7 with 8 M aqueous sodium hydroxide. Sodium borohydride (28 g) was added to the mixture and dissolved, and then the mixture was stirred overnight. The reaction mixture was adjusted to pH 5.5 with acetic acid under ice cooling, and stirred at 4° C. for 1 hour. The mixture was adjusted to pH 7.5 with 8 M aqueous sodium hydroxide. The resulting aqueous solution was desalted by ultrafiltration using a Biomax-50 membrane. The residual solution, which did not pass through the membrane, was lyophilized to obtain dextran polyalcohol (10.5 g). The molecular weight (gel filtration, pullulan standard) of the resulting product was 159K.

The resulting dextran polyalcohol (7.5 g) was added to an aqueous solution obtained by dissolving sodium hydroxide (315 g) in water (225 ml), and dissolved at room temperature. Monochloroacetic acid (45 g was added to the solution under ice cooling and dissolved, and the mixture was allowed to react at room temperature overnight. The reaction mixture was adjusted to pH 8 with acetic acid, and desalted by ultrafiltration using a Biomax-50 membrane. The residual solution, which did not pass through the membrane, was lyophilized to obtain sodium salt of carboxymethyldextran polyalcohol (8.5 g). The molecular weight (gel filtration, pullulan standard) of the resulting product was 274K, and the carboxymethylation degree thereof was 0.4.

1-Ethyl-3-(3-dimethylaminopropyl)carbodiimide (571 mg) was added to a mixture of Boc-Gly-Gly-Gly-Phe-OH SEQ ID NO: 2) (1,000 mg), 4-aminobenzyl alcohol (324 mg), 1-hydroxybenzotriazole (464 mg) and N,N-dimethylformamide (10 ml). The resulting mixture was allowed to react with stirring at room temperature overnight, and then the reaction mixture was evaporated to dryness under reduced pressure. The residue was purified by silica gel column chromatography (eluate: a solution of dichloromethane:methanol=92:8) to obtain Compound 2b (1,220 mg).

$^1$H-NMR (DMSO-d$_6$)δ: 9.91 (s, 1H), 8.25 (d, 1H, J=3.7 Hz), 8.08–8.20 (m, 2H), 7.54 (d, 2H, J=8.3 Hz), 7.25–7.29 (m, 4H), 7.23 (d, 2H, J=8.3 Hz), 7.16–7.21 (m, 1H), 6.95 (t, 1H, J=5.9 Hz), 5.08 (d, 1H, J=5.9 Hz), 4.62–4.67 (m, 1H), 4.44 (d, 2H, J=5.9 Hz), 3.74 (dd, 1H, J=4.9, 5.4 Hz), 3.65 (dd, 1H, J=5.9, 16.6 Hz), 3.59 (d, 2H, J=5.4 Hz), 3.07 (dd, 1H, J=5.4, 13.7 Hz), 2.90 (dd, 1H, J=9.3, 13.7 Hz), 1.37 (s, 9H).

A mixture of Compound 2b (1,160 mg), bis(4-nitrophenyl)carbonate (1,303 mg), diisopropylethylamine (0.555 ml), 4-(dimethylamino)pyridine (26 mg) and tetrahydrofuran (0 ml) was allowed to react with stirring at room temperature for 4 days. Then, the reaction mixture was evaporated to dryness under reduced pressure. The residue was purified by silica gel column chromatography (eluate: a solution of dichloromethane:methanol=96:4) to obtain Compound 3b (650 mg).

$^1$H-NMR (DMSO-d$_6$)δ: 10.07 (s, 1H), 8.31 (d, 1H, J=8.8 Hz), 8.24–8.25 (m, 1H). 8.09–8.12 (m, 2H), 7.65 (d, 2H, J=8.3 Hz), 7.56 (d, 2H, J=8.8 Hz), 7.42 (d, 2H, J=8.3 Hz), 7.27–7.28 (m, 5H), 7.18–7.19 (m, 1H), 6.95 (s, 1H), 5.68–5.73 (m, 1H), 5.25 (s, 2H), 4.64–4.69 (m, 1H), 3.58–3.79 (m, 6H), 3.08 (dd, 1H, J=4.9, 13.7 Hz), 2.91 (dd, 1H, J=9.8, 13.7 Hz), 1.37 (s, 9H).

A mixture of Compound 3b (576 mg), methanesulfonate of DX-8951 (497 mg), 1-hydroxybenzotriazole (113 mg), diisopropylethylamine (0.303 ml) and N,N-dimethylformamide (10 ml) was allowed to react with stirring at room temperature overnight. Then, the reaction mixture was evaporated to dryness under reduced pressure. The residue was purified by silica gel column chromatography (eluate: a solution of dichloromethane:methanol=92:8 containing 0.5% acetic acid) to obtain Compound 4b (290 mg).

$^1$H-NMR (DMSO-d$_6$)δ: 10.01 (s, 1H), 8.24 (d, 1H, J=9.8 Hz), 8.09–8.13 (m, 2H), 8.05 (d, 1H, J=8.8 Hz), 7.74 (d, 1H, J=10.7 Hz), 7.61 (d, 2H, J=8.3 Hz), 7.37 (d, 2H, J=8.3 Hz), 7.32 (s, 1H), 7.24–7.27 (m, 4H), 7.17–7.19 (m, 1H), 6.94 (s, 1H), 5.47 (d, 1H, J=16.1 Hz), 5.42 (d, 1H, J=16.1 Hz), 5.31 (d, 1H, J=19.5 Hz), 5.27–5.29 (m, 1H), 5.24 (d, 1H, J=16.1 Hz), 5.09 (s, 2H), 4.62–4.67 (m, 1H), 3.73–3.78 (m, 2H), 3.66 (d, 1H, J=6.4 Hz), 3.63 (d, 1H, J=5.4 Hz). 3.53–3.59 (m, 2H), 3.23–3.27 (m, 2H), 3.07 (dd, 1H, J=4.9, 13.7 Hz), 2.90 (dd, 1H, J=9.8, 13.7 Hz), 2.37 (s, 3H), 2.17–2.23 (m, 2H), 1.81–1.90 (m, 2H), 1.36 (s, 9H), 0.89 (d, 1H, J=6.8 Hz).

Compound 4b (200 mg) was dissolved in formic acid (4 ml) and allowed to stand for 2 hours. The reaction mixture was added dropwise to ether (40 ml). The precipitate was washed with ether to obtain 198 mg of Compound 5b.

$^1$H-NMR (DMSO-d$_6$)δ: 10.06 (s, 1H), 8.20–8.41 (m, 3H), 8.07 (d, 1H, J=8.7 Hz), 7.75 (t, 1H, J=7.8 Hz), 7.61 (d, 2H, J=8.3 Hz), 7.37 (d, 2H, J=8.3 Hz), 7.32 (s, 1H), 7.21–7.30 (m, 5H), 7.18–7.20 (m, 1H), 5.41–5.48 (m, 2H), 5.23–5.33 (m, 3H), 5.08 (s, 2H), 4.62–4.66 (m, 1H), 3.77 (s, 2H), 3.72–3.76 (m, 1H), 3.63 (dd, 1H, J=5.0, 16.5 Hz), 3.58–3.60 (m, 1H), 3.40 (dd, 1H, J=6.9, 13.7 Hz), 3.20–3.23 (m, 1H), 3.10–3.13 (m, 1H), 3.06 (dd, 1H, J=5.0, 13.7 Hz), 2.90 (dd, 1H, J=9.6, 13.7 Hz), 2.37 (s, 3H), 2.15–2.22 (m, 2H), 1.84–1.90 (m, 2H), 0.88 (d, 1H, J=6.9 Hz).

Compound 5b (100 mg) was dissolved in water (5 ml) and methanol (10 ml). The solution was added to a solution obtained by dissolving the sodium salt of carboxymethyl-dextran polyalcohol obtained in Example 1 (1, 100 mg) in water (10 ml) and methanol (20 ml). The resulting mixture was added with 1-hydroxybenzotriazole (15 mg) and 1-ethyl-3-(3-dimethylaminopropyl)carbodiimide (26 mg), and then adjusted to pH 7.0 with 0.1 N aqueous sodium hydroxide. The mixture was stirred at room temperature for 2 hours, then added with 1-ethyl-3-(3-dimethylaminopropyl)carbodiimide (25 mg). The mixture was stirred at room temperature for 1.5 hours, then added with 1-ethyl-3-(3-dimethylaminopropyl)carbodiimide (13 mg), and allowed to react at room temperature overnight. The reaction mixture was adjusted to pH 8.5 with 0.1 N aqueous sodium hydroxide, and then desalted by ultrafiltration using a Biomax-50 membrane. The residual solution, which did not pass through the membrane, was filtered through a Millipore filter (0.22 μm), and lyophilized. The resulting amorphous was purified with Sep-Pak C$_{18}$ cartridge (Waters Co.) and a Bio-Rad AG50W-X8 (Na$^-$ form) column, and further desalted by ultrafiltration using a Biomax-50 membrane. The residual solution, which did not pass through the membrane, was filtered through a Millipore filter (0.22 μm), and lyophilized to obtain Compound 6b (405 mg). The content of the drug compound residue in the compound was found as 1.7% (w/w) by quantitative analysis based on absorption spectrophotometry at 366 nm in 0.1 M Tris buffer (pH 10.0):acetonitrile=7:3.

Example 7

Synthesis of carboxymethyldextran polyalcohol-Gly-Gly-NH-p-C$_6$H$_4$—CH$_2$—O—CO-DX-8951 Using Formic Acid as a Deprotecting Agent Dextran T500 (20 g, Pharmacia, molecular weight: 500K) was dissolved in 0.1 M acetic buffer (pH 5.5, 2,000 ml), and added with an aqueous solution (2,000 ml) of sodium periodate (66.0 g). The mixture was stirred at 4° C. for 10-days with shielding from the light. Then, the mixture was added with ethylene glycol (14.0 ml) and stirred overnight. The reaction mixture was adjusted to pH 7 with 8 M aqueous sodium hydroxide. Sodium borohydride (28 g) was added to the mixture and dissolved, and then the mixture was stirred overnight. The reaction mixture was adjusted to pH 5.5 with acetic acid under ice cooling, and stirred at 4° C. for 1 hour. The mixture was adjusted to pH 7.5 with 8 M aqueous sodium hydroxide. The resulting aqueous solution was desalted by ultrafiltration using a Biomax-50 membrane. The residual solution, which did not pass through, the membrane, was lyophilized to obtain dextran polyalcohol (10.5 g). The molecular weight (gel filtration, pullulan standard) of the resulting product was 159K.

The resulting dextran polyalcohol (7.5 g) was added to an aqueous solution obtained by dissolving sodium hydroxide (31.5 g) in water (225 ml), and dissolved at room temperature. Monochloroacetic acid (45 g) was added to the solution under ice cooling and dissolved, and the mixture was allowed to react at room temperature overnight. The reaction mixture was adjusted to pH 8 with acetic acid, and desalted by ultrafiltration using a Biomax-50 membrane. The residual solution, which did not pass through the membrane, was lyophilized to obtain sodium salt of carboxymethyldextran-polyalcohol (8.5 g). The molecular weight (gel filtration, pullulan standard) of the resulting product was 274K, and the carboxymethylation degree thereof was 0.4.

1-Ethyl-3-(3-dimethylaminopropyl)carbodiimide (4.05 g) was added to a mixture of Boc-Gly-Gly-OH (2.3 g), 4-aminobenzyl alcohol (2.0 g), 1-hydroxybenzotriazole (3.29 g) and N,N-dimethylformamide (20 ml). The resulting mixture was allowed to react with stirring at room temperature overnight, and then the reaction mixture was evaporated to dryness under reduced pressure. The residue was purified by silica gel column chromatography (eluate: a solution of dichloromethane:methanol=94:6) to obtain Compound 2c (2.9 g).

$^1$H-NMR (DMSO-$d_6$)δ: 9.75 (s, 1H), 8.15 (s, 1H), 7.54 (d, 2H, J=8.3 Hz), 7.23 (d, 2H, J=8.3 Hz), 7.07 (s, 1H), 5.09 (t, 1H, J=8.6 Hz), 4.44 (d, 2H, J=8.6 Hz), 3.88 (s, 2H), 3.60 (s, 1H), 1.39 (s, 9H).

A mixture of Compound 2c (1.0 g), bis(4-nitrophenyl) carbonate (2.72 g), diisopropylethylamine (1.17 ml), 4(dimethylamino)pyridine (55 mg) and tetrahydrofuran (50 ml) was allowed to react with stirring at room temperature for 3 days. Then, the reaction mixture was evaporated to dryness under reduced pressure. The residue was purified by silica gel column chromatography (eluate: a solution of dichloromethane:methanol=96:4) to obtain Compound 3c (376 mg).

$^1$H-NMR (DMSO-$d_6$)δ: 9.92 (s, 1H), 8.31 (d, 1H, J=9.3 Hz), 8.14–8.25 (m, 2H), 7.65 (d, 2H, J=8.3 Hz), 7.56 (d, 2H, J=9.3 Hz), 7.41 (d, 2H, J=8.3 Hz), 7.06 (d, 1H, J=5.4 Hz), 5.25 (s, 2H), 3.91 (d, 2H, J=4.9 Hz), 3.61 (d, 2H, J=5.4 Hz), 1.40 (s, 9H).

A mixture of Compound 3c (338 mg), methanesulfonate of DX-8951 (400 mg), 1-hydroxybenzotriazole (109 mg), diisopropylethylamine (0.243 ml) and N,N-dimethylformamide (20 ml) was allowed to react with stirring at room temperature overnight. Then, the reaction mixture was evaporated to dryness under reduced pressure. The residue was purified by silica gel column chromatography (eluate: a solution of dichloromethane:methanol=94:6 containing 0.5% acetic acid) to obtain Compound 4c (460 mg).

$^1$H-NMR (DMSO-$d_6$) δ: 9.84 (s, 1H), 8.13–8.15 (m, 1H), 8.04 (d, 1H, J=8.8 Hz), 7.73 (d, 1H, J=10.7 Hz), 7.60 (d, 2H, J=8.3 Hz), 7.37 (d, 2H, J=8.3 Hz), 7.32 (s, 1H), 7.04 (d, 1H), J=5.9 Hz), 6.48 (s, 1H), 5.46 (d, 1H, J=16.1 Hz), 5.41 (d, 1H, J=16.1 Hz), 5.31 (d, 1H, J=19.0 Hz), 5.26–5.29 (m, 1H, 5.24 (d, 1H, J=19.0 Hz), 5.08 (s, 2H), 3.90 (d, 2H, J=4.9 Hz), 3.61 (d, 2H, J=5.9 Hz), 3.07–3.12 (m, 2H), 2.37 (s, 3H), 2.15–2.23 (m, 2H), 1.83–1.92 (m, 2H), 1.39 (s, 9H), 0.89 (d, 1H, J=7.3 Hz).

Compound 4c (100 mg) was dissolved in formic acid (4 ml) and allowed to stand for 2 hours. The reaction mixture was added dropwise to ether (40 ml). The precipitate was washed with ether to obtain Compound 5c (98 mg).

$^1$H-NMR (DMSO-$d_6$)δ: 10.02 (s, 1H); 8.24–8.30 (m, 3H), 8.05–8.09 (m, 1H), 7.73–7.76 (m, 2H), 7.59 (d, 2H, J=6.6 Hz), 7.34–7.38 (m, 3H), 6.51 (s, 1H), 5.41–5.49 (m, 2H), 5.24–5.31 (m, 3H), 5.08 (s, 2H), 3.95 (s, 2H), 3.28 (s, 2H), 3.07–3.14 (m, 2H), 2.39 (s, 3H), 2.14–2.28 (m, 2H), 1.86–1.90 (m, 2H), 0.90 (d, 1H, J=6.0 Hz).

Figure 5:
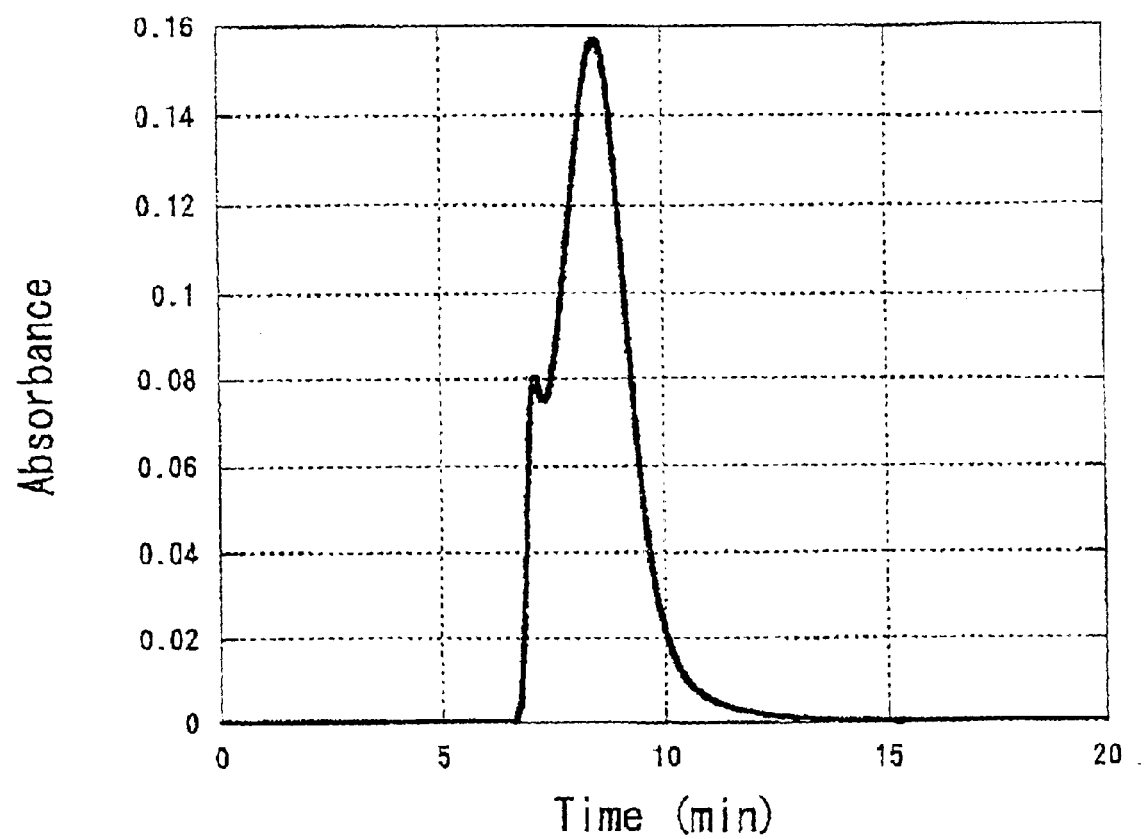
FIG. 5 shows a GPC chart of the drug complex of the present invention (Example 7).
Figure 6:
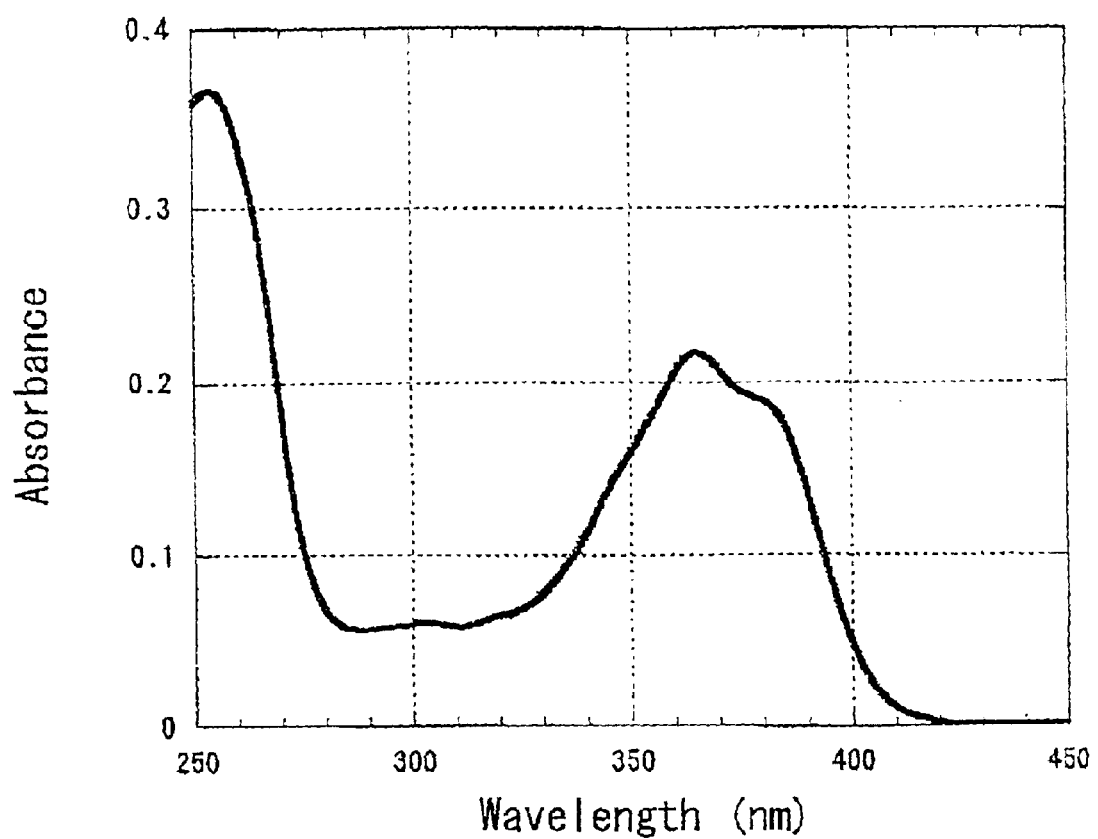
FIG. 6 shows an ultraviolet absorption spectrum of the drug complex of the present invention (Example 7).

Compound 6c (95 mg) was dissolved in water (15 ml) and methanol (15 ml). The solution was added to a solution obtained by dissolving the sodium salt of carboxymethyl-dextran polyalcohol obtained in Example 1 (1,000 mg) in water (15 ml) and methanol (15 ml). The resulting mixture was added with 1-hydroxybenzotriazole (28 mg) and 1-ethyl-3-(3-dimethylaminopropyl)carbodiimide (53 mg), and then adjusted to pH 7.0 with 0.1 N aqueous sodium hydroxide. The mixture was stirred at room temperature for 3 hours, then added with 1-ethyl-3(3-dimethylaminopropyl) carbodiimide (26 mg). The mixture was stirred at room temperature for 1.5 hours, then added with 1-ethyl-3(3-dimethylaminopropyl)carbodiimide (12 mg), and allowed to react at room temperature overnight. The reaction mixture was adjusted to pH 8.5 with 0.1 N aqueous sodium hydroxide, and then desalted by ultrafiltration using a Biomax-50 membrane. The residual solution, which did not pass through the membrane, was filtered through a Millipore filter (0.22 μm), and lyophilized. The resulting amorphous was purified with Sep-Pak $C_{18}$ cartridge (Waters Co.) and a Bio-Rad AG50W-X8 (Na⁻ form) column, and further desalted by ultrafiltration using a Biomax-50 membrane. The residual solution, which did not pass through the membrane, was filtered through a Millipore filter (0.22 μm), and lyophilized to obtain Compound 6c (588 mg). This compound was dissolved in 0.1 M aqueous sodium chloride, and analyzed by GPC (column: TOSOH TSX Gel PW-4000XL, solvent: 0.1 M aqueous NaCl containing 20% acetonitrile, flow rate: 0.8 ml/min). The results of the GPC analysis and an ultraviolet absorption spectrum (0.1 M Tris buffer, pH 9.0, 0.12 mg/ml) of the compound are shown in FIGS. 5 and 6, respectively. The content of the drug compound residue in the compound was found as 3.3% (w/w) by quantitative analysis based on absorption spectrophotometry at 366 nm in 0.1 M Tris buffer (pH 10.0):acetonitrile=7:3.

Example 8

Release of the Drug Compound from the Drug Complex

The drug complexes obtained in Examples 6, 6 and 7 were dissolved, respectively, in a Meth A (murine fibrosarcoma Meth A) homogenate or a buffer at 37° C. (50 μg/ml). After 20 hours, the released DX-8961 was determined. A compound wherein the spacer and DX-8951 were bound to each other without p-aminobenzyloxycarbonyl group was prepared and used as a comparative compound. The result is shown in Table 4. The released amount of the drug is expressed in percentage of the released amount of the drug to the amount of the drug in the drug complex used. The drug complexes of Examples 5, 6 and 7 were rapidly released in the weakly acidic homogenate, but hardly released in the buffer. On the ocher band, the comparative compound was released in a slight amount in the weakly acidic homogenate, but not released in the buffer.

TABLE 4

|  | Ex. 5 | Ex. 6 | Ex. 7 | Comparative compound |
|---|---|---|---|---|
| Meth A homogenate (pH 4.5) | 110.69 | 15.48 | 0.44 | 0.85 |
| Meth A homogenate (pH 5.5) | 110.31 | 4.97 | 0.37 | 0.12 |
| Meth A homogenate (pH 6.5) | 42.71 | 1.78 | 0.55 | 0.01 |
| Buffer (pH 4.5) | 0.79 | 0.12 | 0.15 | 0.00 |
| Buffer (pH 5.5) | 0.71 | 0.19 | 0.12 | 0.00 |
| Buffer (pH 6.5) | 0.8 | 0.23 | 0.16 | 0.00 |
| Plasma | 0.13 | 0.51 | 0.12 | 0.00 |

Example 9

Maximum Tolerated Dose (ITD) of the Drug Complexes of Examples 5, 6 and 7 to Meth A Tumor-bearing Mice Meth A cells were transplanted into BALB/c mice to prepare Meth A tumor-bearing mice. On the 13th day, the drug complexes obtained in Examples 5, 6 and 7 were singly administered. After the administration, measurement of the body weight and observation of toxic death were made with time, and the maximum body-weight reduction rate and mortality were calculated, which are shown in Table 5. The dose is expressed in terms of the weight of anhydrous free base of DX-8951.

TABLE 5

| Compound | Dose (mg/kg) | BWLmax$^a$ (%)[day] | N$^b$ |
|---|---|---|---|
| Control | 0 | <0 | 0/3 |
| Example 5 | 10 | 27.1[18] | 3/3 |
|  | 5 | 28.6[18] | 3/3 |
|  | 2.5 | 28.9[20] | 3/3 |
|  | 1.25 | 5.0[18] | 0/3 |
|  | 0.625 | 2.0[14] | 0/3 |
| Example 6 | 10 | 27.1[18] | 3/3 |
|  | 5 | 24.0[18] | 3/3 |
|  | 2.5 | 22.1[20] | 0/3 |
|  | 1.25 | 2.4[14] | 0/3 |
| Example 7 | 30 | 14.6[16] | 3/3 |
|  | 20 | 14.2[16] | 3/3 |
|  | 10 | 13.7[16] | 3/3 |
|  | 5 | 25.4[18] | 3/3 |
|  | 2.5 | 31.0[21] | 3/3 |

$^a$The maximum body-weight reduction rate (The numbers in the parentheses are the days when the maximum reduction was observed.)
<0 means that reduction of the body weight was not observed.
$^b$Mice died/mice used On the basis of the dose in which body weight reduction and death were observed, MTD of each complex were judged as follows.

TABLE 6

|  | MTD (mg/kg) |
|---|---|
| Example 5 | 1.25~2.5 |
| Example 6 | 2.5 |
| Example 7 | <2.5 |

MTD of the drug complex obtained in Example 5 was about ⅓ of MTD of the drug complex obtained in Example 1 (see Example 3). The result was found to be correlated with the fact that, when the drug complex obtained in Example 1 was used (see the table in Example 2), the releasing rate of DX-8951 was about 113 of the releasing rate of DX-8951 when the drug complex obtained in Example 5 was used (see the table in Example 8).

Example 10

Antineoplastic Activity of the Complexes Shown in Examples 5 and 6

Meth A cells were transplanted into BALB/c mice to prepare Meth A tumor-bearing mice. On the 7th day after the transplantation, the drug complexes shown in Examples 1, 5 and 6 were singly administered, respectively. The weight of the tumor was measured on the 21th day to evaluate the inhibitory activity on the tumor and the toxicity. The results are shown in Table 7. In the table, * represents significance in Dunnet's test (* p<0.001,  P<0.01, * P<0.05), the dose is expressed in terms of the weight of anhydrous free base of DX-8951, and IR represents the diminution rate of the tumor. The drug complexes shown in Examples 5 and 6 are found to exhibit dose-dependent tumor-diminution activity.

In addition, the minimal effective dose of the drug complex shown in Example 5 was about ⅓ of that of the drug complex shown in Example 1. The result was found to be correlated with the fact that similar difference was observed between the releasing rate of DX-8961 in the neoplastic homogenates (see the tables in Examples 2 and 8) and MTD in the Meth A tumorbearing mice (see the tables in Examples 3 and 9).

TABLE 7

| Compound | Dose (mg/kg) | Average tumor weight (g) | IR(%) | BWLmax$^a$ (%)[day] | N$^b$ |
|---|---|---|---|---|---|
| Control | 0 | 2.624 ± 0.417 | 0 | <0 | 0/6 |
| Example 1 | 7.5 | 0.005 ± 0.003*** | 100 | 26.1[16] | 2/6 |
|  | 5 | 0.004 ± 0.001*** | 100 | 4.0[13] | 0/6 |
|  | 2.5 | 0.031 ± 0.014*** | 99 | <0 | 0/6 |
|  | 1.25 | 0.775 ± 0.207*** | 71 | <0 | 0/6 |
|  | 0.625 | 1.489 ± 0.215** | 43 | <0 | 0/6 |
| Example 5 | 1.875 | 0.011 ± 0.003*** | 100 | 12.3[13] | 0/6 |
|  | 1.25 | 0.010 ± 0.004*** | 100 | <0 | 0/6 |
|  | 0.625 | 0.328 ± 0.164*** | 88 | <0 | 0/6 |
|  | 0.3125 | 1.128 ± 0.173*** | 57 | <0 | 0/6 |
|  | 0.15625 | 2.394 ± 0.231 | 9 | <0 | 0/6 |
| Example 6 | 2.5 | 0.012 ± 0.004*** | 100 | 25.9[13] | 3/6 |
|  | 1.25 | 0.016 ± 0.008*** | 99 | <0 | 0/6 |
|  | 0.625 | 0.272 ± 0.066*** | 90 | <0 | 0/6 |
|  | 0.3125 | 1.419 ± 0.163** | 46 | <0 | 0/6 |
|  | 0.15625 | 1.645 ± 0.191* | 37 | <0 | 0/6 |

$^a$The maximum body-weight reduction rate (The numbers in the parentheses are the days when the maximum reduction was observed.)
<0 means that reduction of the weight was not observed.
$^b$Mice died/mice used

INDUSTRIAL APPLICABILITY

The drug complex of the present invention can site-selectively transfer a drug compound such as antineoplastic agents and anti-inflammatory agents to a tumorous site and the like and rapidly release the drug compound at the site. In addition, the drug complex is characterized to surely exhibit expected efficacy of the drug compound, since no amino acid derived from the spacer moiety remains in the released drug compound.

What is claimed is:

1. A drug complex represented by the following formula:

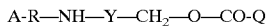
A-R—NH—Y—CH$_2$—O—CO-Q wherein A is a polymer as a drug carrier comprising a polysaccharide derivative having carboxyl groups; R is a spacer, wherein said spacer is an amino acid or an oligopeptide comprising 2 to 8 amino acids; Y is phenylene group which may be substituted; and Q is a residue of a drug compound.

2. The drug complex according to claim 1, wherein R is a spacer comprising peptide-bonded 2 to 8 amino acids.

3. The drug complex according to claim 1, wherein Y is p-phenylene group which may be substituted.

4. The drug complex according to claim 1, wherein Y is unsubstituted p-phenylene group.

5. The drug complex according to claim 1, wherein the polysaccharide derivative having carboxyl groups is a carboxy($C_{1-4}$)alkyldextran polyalcohol.

6. The drug complex according to claim 5, wherein dextran polyalcohol that constitutes the carboxy($C_{1-4}$) alkyldextran polyalcohol is dextran polyalcohol which is obtained by treating dextran under conditions that enable substantially complete polyalcoholization.

7. The drug complex according to claim 5, wherein the carboxy($C_{1-4}$)alkyldextran polyalcohol is carboxymethyl-dextran polyalcohol.

8. The drug complex according to claim 1, wherein the drug compound is an antineoplastic agent or an anti-inflammatory agent.

9. The drug complex according to claim 1, wherein the drug compound has an amino group and the amino group is bound to A-R—NH—Y—CH$_2$—O—CO— by the amino group.

10. The drug complex according to claim 9, wherein the drug compound is (1S,9S)-1-amino-9-ethyl-5-fluoro-2,3-dihydro-9-hydroxy-4-methyl-1H,12H-benzo[de]-pyrano[3', 4':6,7]indolizino[1,2-b]quinoline-10,13(9H,15H)-dione.

11. The drug complex according to claim 10, wherein R is -Gly-Gly-Phe-Gly- (SEQ ID NO: 1).

12. The drug complex according to claim 10, wherein R is -Gly-Gly-Gly-Phe- (SEQ ID NO: 2).

13. A drug delivery system composition comprising a drug complex according to claim 1.

14. The drug delivery system composition according to claim 13, wherein the drug compound is (1S,9S)-1-amino-9-ethyl-5-fluoro-2,3-dihydro-9-hydroxy-4-methyl-1H, 12H-benzo[de]pyrano[3',4':6,7]indolizino[1,2-b]quinoline-10, 13-(9H,15H)-dione.

15. The drug delivery system composition according to claim 14, wherein R is -Gly-Gly-Phe-Gly- (SEQ ID NO: 1).

16. The drug delivery system according to claim 14, wherein R is -Gly-Gly-Gly-Phe- (SEQ ID NO: 2).

17. A method of producing a drug complex according to claim 1, comprising reacting a compound represented by the following formula with a drug compound:

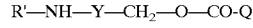
R'—NH—Y—CH$_2$—O—CO-Q wherein R' is a group which comprises one amino acid or peptide-bonded 2 to 8 amino acids and whose N-terminal is protected or not protected; Y is phenylene group which may be substituted; and Q is a residue of a drug compound.

18. The method according to claim 17, wherein Y is unsubstituted p-phenylene group, R' is a group represented by H-Gly-Gly-Phe-Gly- (SED ID NO: 1), and the drug compound is (1S,9S)-1-amino-9-ethyl-5-fluoro-2,3-dihydro-9-hydroxy-4-methyl-1H,12H-benzo[de]pyrano[3', 4':6,7]indolizino[1,2-b]quinoline-10,13-(9H, 15H)-dione.

19. The method according to claim 17, wherein Y is unsubstituted p-phenylene group, R' is a group represented by H-Gly-Gly-Gly-Phe- (SEQ ID NO: 2), and the drug-compound is (1S,9S)-1-amino-9-ethyl-5-fluoro-2,3-dihydro-9-hydroxy-4-methyl-1H,12H-benzo[de]pyrano[3', 4':6,7]indolizino[1,2-b]quinoline-10,13(9H,15H)-dione.

20. A compound represented by the following formula:

A-R—NH—Y—CH$_2$—O—CO—X wherein A is a polymer as a drug carrier; R is a spacer, wherein said spacer is an amino acid or an oligopeptide comprising 2 to 8 amino acids; Y is phenylene group which may be substituted; and X is selected from the group comprising hydroxyl group, —O-M wherein M is a protective group for carboxyl group, or an eliminating group.

* * * * *

UNITED STATES PATENT AND TRADEMARK OFFICE
CERTIFICATE OF CORRECTION

PATENT NO. : 6,835,807 B1
DATED : December 28, 2004
INVENTOR(S) : H. Susaki et al.

It is certified that error appears in the above-identified patent and that said Letters Patent is hereby corrected as shown below:

<u>Title page,</u>
Item [56], References Cited, FOREIGN PATENT DOCUMENTS, should include
-- 00/25825     5/11/00     W.I.P.O. --.

Signed and Sealed this

Twenty-seventh Day of September, 2005

JON W. DUDAS
*Director of the United States Patent and Trademark Office*

SEQUENCE LISTING

<160> NUMBER OF SEQ ID NOS: 2

<210> SEQ ID NO 1
<211> LENGTH: 4
<212> TYPE: PRT
<213> ORGANISM: Artificial
<220> FEATURE:
<223> OTHER INFORMATION: Spacer Sequence

<400> SEQUENCE: 1

Gly Gly Phe Gly
1

<210> SEQ ID NO 2
<211> LENGTH: 4
<212> TYPE: PRT
<213> ORGANISM: Artificial
<220> FEATURE:
<223> OTHER INFORMATION: Spacer Sequence

<400> SEQUENCE: 2

Gly Gly Gly Phe
1